(12) United States Patent
Koseoglu et al.

(10) Patent No.: US 11,320,413 B1
(45) Date of Patent: May 3, 2022

(54) CHARACTERIZATION OF CRUDE OIL BY TIME OF FLIGHT MASS SPECTROMETRY

(71) Applicant: SAUDI ARABIAN OIL COMPANY, Dhahran (SA)

(72) Inventors: Omer Refa Koseoglu, Dhahran (SA); Adnan Al-Hajji, Dhahran (SA); Hendrik Muller, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 0 days.

(21) Appl. No.: 17/183,872

(22) Filed: Feb. 24, 2021

(51) Int. Cl.
| | | |
|---|---|---|
| *G01N 33/00* | (2006.01) | |
| *G01N 33/24* | (2006.01) | |
| *H01J 49/00* | (2006.01) | |
| *H01J 49/40* | (2006.01) | |

(52) U.S. Cl.
CPC ........ *G01N 33/241* (2013.01); *H01J 49/0036* (2013.01); *H01J 49/408* (2013.01)

(58) Field of Classification Search
CPC ... G01N 33/241; H01J 49/0036; H01J 49/408
USPC ................................ 250/281, 282, 287, 288
See application file for complete search history.

(56) References Cited

U.S. PATENT DOCUMENTS

| | | |
|---|---|---|
| 6,633,043 B2 | 10/2003 | Hegazi et al. |
| 7,598,487 B2 | 10/2009 | Qian et al. |
| 8,992,770 B2 | 3/2015 | Gong et al. |
| 9,285,307 B2 | 3/2016 | Koseoglu et al. |
| 9,429,556 B2 | 8/2016 | Koseoglu |
| 9,778,240 B2 | 10/2017 | Koseoglu et al. |
| 9,816,919 B2 | 11/2017 | Koseoglu et al. |
| 10,031,121 B2 | 7/2018 | Koseoglu et al. |
| 10,048,194 B2 | 8/2018 | Koseoglu et al. |
| 10,345,285 B2 | 7/2019 | Koseoglu et al. |
| 10,401,344 B2 | 9/2019 | Koseoglu et al. |
| 10,527,546 B2 | 1/2020 | Koseoglu et al. |
| 10,571,452 B2 | 2/2020 | Koseoglu et al. |
| 10,627,345 B2 | 4/2020 | Koseoglu et al. |
| 10,677,718 B2 | 6/2020 | Koseoglu et al. |
| 10,684,239 B2 | 6/2020 | Koseoglu et al. |
| 10,725,013 B2 | 7/2020 | Koseoglu et al. |
| 10,794,821 B2 | 10/2020 | Koseoglu et al. |
| 10,845,355 B2 | 11/2020 | Koseoglu |
| 10,928,375 B2 | 2/2021 | Al-Hajji et al. |
| 10,942,160 B2 | 3/2021 | Koseoglu et al. |
| 11,022,588 B2 * | 6/2021 | Koseoglu ........... G01N 33/2823 |
| 2017/0363591 A1 * | 12/2017 | Koseoglu ........... G01N 33/2823 |
| 2018/0307803 A1 | 10/2018 | Watanasiri et al. |
| 2020/0116683 A1 | 4/2020 | Koseoglu et al. |

(Continued)

OTHER PUBLICATIONS

Coutinho, D., et al., "Rapid hydrocarbon group-type semi-quantification in crude oils by comprehensive two-dimensional gas chromatography", Fuel 220 (2018) 379-388.

(Continued)

*Primary Examiner* — Michael Maskell
(74) *Attorney, Agent, or Firm* — Leason Ellis LLP

(57) ABSTRACT

A system and computer program product are provided for calculating one or more indicative properties, e.g., one or more of the cetane number, octane number, pour point, cloud point, octane number, and aniline point of oil fractions, from the density and time of flight mass spectrometry (TOF-MS) of a sample of an oil sample.

20 Claims, 6 Drawing Sheets

(56) References Cited

U.S. PATENT DOCUMENTS

2020/0400645 A1* 12/2020 Muller ................ G01N 33/287

OTHER PUBLICATIONS

Vanini, G., et al., "Analytical advanced techniques in the molecular-level characterization of Brazilian crude oils", Microchemical Journal 137 (2018) 111-118.
Vale , D., et al., "Comprehensive and multidimensional tools for crude oil property prediction and petrochemical industry refinery inferences", Fuel 223 (2018) 188-197.

* cited by examiner

CHARACTERIZATION OF CRUDE OIL BY TIME OF FLIGHT MASS SPECTROMETRY

BACKGROUND OF THE INVENTION

Field of the Invention

This invention relates to a method and process for the evaluation of samples of crude oil and its fractions by time of flight mass spectrometry (TOF-MS).

Description of Related Art

Crude oil originates from the decomposition and transformation of aquatic, mainly marine, living organisms and/or land plants that became buried under successive layers of mud and silt some 15-500 million years ago. They are essentially very complex mixtures of many thousands of different hydrocarbons. Depending on the source, the oil predominantly contains various proportions of straight and branched-chain paraffins, cycloparaffins, and naphthenic, aromatic, and polynuclear aromatic hydrocarbons. These hydrocarbons can be gaseous, liquid, or solid under normal conditions of temperature and pressure, depending on the number and arrangement of carbon atoms in the molecules.

Crude oils vary widely in their physical and chemical properties from one geographical region to another and from field to field. Crude oils are usually classified into three groups according to the nature of the hydrocarbons they contain: paraffinic, naphthenic, asphaltic, and their mixtures. The differences are due to the different proportions of the various molecular types and sizes. One crude oil can contain mostly paraffins, another mostly naphthenes. Whether paraffinic or naphthenic, one can contain a large quantity of lighter hydrocarbons and be mobile or contain dissolved gases; another can consist mainly of heavier hydrocarbons and be highly viscous, with little or no dissolved gas. Crude oils can also include heteroatoms containing sulfur, nitrogen, nickel, vanadium and other elements in quantities that impact the refinery processing of the crude oil fractions. Light crude oils or condensates can contain sulfur in concentrations as low as 0.01 W %; in contrast, heavy crude oils can contain as much as 5-6 W %. Similarly, the nitrogen content of crude oils can range from 0.001-1.0 W %.

The nature of the crude oil governs, to a certain extent, the nature of the products that can be manufactured from it and their suitability for special applications. A naphthenic crude oil will be more suitable for the production of asphaltic bitumen, a paraffinic crude oil for wax. A naphthenic crude oil, and even more so an aromatic one, will yield lubricating oils with viscosities that are sensitive to temperature. However, with modern refining methods there is greater flexibility in the use of various crude oils to produce many desired type of products.

A crude oil assay is a traditional method of determining the nature of crude oils for benchmarking purposes. Crude oils are subjected to true boiling point (TBP) distillations and fractionations to provide different boiling point fractions. The crude oil distillations are carried out using the American Standard Testing Association (ASTM) Method D 2892. The common fractions and their nominal boiling points are given in Table 1.

TABLE 1

| Fraction | Boiling Point, °C. |
|---|---|
| Methane | −161.5 |
| Ethane | −88.6 |
| Propane | −42.1 |
| Butanes | −6.0 |
| Light Naphtha | 36-90 |
| Mid Naphtha | 90-160 |
| Heavy Naphtha | 160-205 |
| Light Gas Oil | 205-260 |
| Mid Gas Oil | 260-315 |
| Heavy Gas Oil | 315-370 |
| Light Vacuum Gas Oil | 370-430 |
| Mid Vacuum Gas Oil | 430-480 |
| Heavy Vacuum Gas Oil | 480-565 |
| Vacuum Residue | 565+ |

The yields, composition, physical and indicative properties of these crude oil fractions, where applicable, are then determined during the crude assay work-up calculations. Typical compositional and property information obtained from a crude oil assay is given in Table 2.

TABLE 2

| Property | Unit | Property Type | Fraction |
|---|---|---|---|
| Yield Weight and Volume % | W % | Yield | All |
| API Gravity | ° | Physical | All |
| Viscosity Kinematic @ 38° C. | ° | Physical | Fraction boiling >250 °C. |
| Refractive Index @ 20° C. | Unitless | Physical | Fraction boiling <400 °C. |
| Sulfur | W % | Composition | All |
| Mercaptan Sulfur, W% | W % | Composition | Fraction boiling <250 °C. |
| Nickel | PPmw | Composition | Fraction boiling >400 °C. |
| Nitrogen | PPmw | Composition | All |
| Flash Point, COC | °C. | Indicative | All |
| Cloud Point | °C. | Indicative | Fraction boiling >250 °C. |
| Pour Point, (Upper) | °C. | Indicative | Fraction boiling >250 °C. |
| Freezing Point | °C. | Indicative | Fraction boiling >250 °C. |
| Microcarbon Residue | W% | Indicative | Fraction boiling >300 °C. |
| Smoke Point, mm | mm | Indicative | Fraction boiling between 150-250 |
| Octane Number | Unitless | Indicative | Fraction boiling <250 °C. |
| Cetane Index | Unitless | Indicative | Fraction boiling between 150-400 |
| Aniline Point | °C. | Indicative | Fraction boiling <520 °C. |

Due to the number of distillation cuts and the number of analyses involved, the crude oil assay work-up is both costly and time consuming.

In a typical refinery, crude oil is first fractionated in the atmospheric distillation column to separate sour gas and light hydrocarbons, including methane, ethane, propane, butanes and hydrogen sulfide, naphtha (36°-180° C.), kerosene (180°-240° C.), gas oil (240°-370° C.) and atmospheric residue (>370° C.). The atmospheric residue from the atmospheric distillation column is either used as fuel oil or sent to a vacuum distillation unit, depending on the configuration of the refinery. The principal products obtained from vacuum distillation are vacuum gas oil, comprising hydrocarbons boiling in the range 370°-520° C., and vacuum residue, comprising hydrocarbons boiling above 520° C. Crude assay data is conventionally obtained from individual analysis of these cuts to help refiners to understand the general composition of the crude oil fractions and properties so that the fractions can be processed most efficiently and effectively in an appropriate refining unit. Indicative properties are used to determine the engine/fuel performance or usability or flow characteristic or composition. A summary of the indicative properties and their determination methods with description is given below.

The cetane number of diesel fuel oil, determined by the ASTM D613 method, provides a measure of the ignition quality of diesel fuel; as determined in a standard single cylinder test engine; which measures ignition delay compared to primary reference fuels. The higher the cetane number; the easier the high-speed; direct-injection engine will start; and the less white smoking and diesel knock after start-up. The cetane number of a diesel fuel oil is determined by comparing its combustion characteristics in a test engine with those for blends of reference fuels of known cetane number under standard operating conditions. This is accomplished using the bracketing hand wheel procedure which varies the compression ratio (hand wheel reading) for the sample and each of the two bracketing reference fuels to obtain a specific ignition delay, thus permitting interpolation of cetane number in terms of hand wheel reading.

The octane number, determined by the ASTM D2699 or D2700 methods, is a measure of a fuel's ability to prevent detonation in a spark ignition engine. Measured in a standard single-cylinder; variable-compression-ratio engine by comparison with primary reference fuels. Under mild conditions, the engine measures research octane number (RON), while under severe conditions, the engine measures motor octane number (MON). Where the law requires posting of octane numbers on dispensing pumps, the antiknock index (AKI) is used. This is the arithmetic average of RON and MON, (R+M)/2. It approximates the road octane number, which is a measure of how an average car responds to the fuel.

The cloud point, determined by the ASTM D2500 method, is the temperature at which a cloud of wax crystals appears when a lubricant or distillate fuel is cooled under standard conditions. Cloud point indicates the tendency of the material to plug filters or small orifices under cold weather conditions. The specimen is cooled at a specified rate and examined periodically. The temperature at which cloud is first observed at the bottom of the test jar is recorded as the cloud point. This test method covers only petroleum products and biodiesel fuels that are transparent in 40 mm thick layers, and with a cloud point below 49° C.

The pour point of petroleum products, determined by the ASTM D97 method, is an indicator of the ability of oil or distillate fuel to flow at cold operating temperatures. It is the lowest temperature at which the fluid will flow when cooled under prescribed conditions. After preliminary heating, the sample is cooled at a specified rate and examined at intervals of 3° C. for flow characteristics. The lowest temperature at which movement of the specimen is observed is recorded as the pour point.

The aniline point, determined by the ASTM D611 method, is the lowest temperature at which equal volumes of aniline and hydrocarbon fuel or lubricant base stock are completely miscible. A measure of the aromatic content of a hydrocarbon blend is used to predict the solvency of a base stock or the cetane number of a distillate fuel. Specified volumes of aniline and sample, or aniline and sample plus n-heptane, are placed in a tube and mixed mechanically. The mixture is heated at a controlled rate until the two phases become miscible. The mixture is then cooled at a controlled rate and the temperature at which two separate phases are again formed is recorded as the aniline point or mixed aniline point.

To determine these properties of gas oil or naphtha fractions conventionally, these fractions have to be distilled from the crude oil and then measured/identified using various analytical methods that are laborious, costly and time-consuming.

TOF-MS includes two components: an ionization source and a mass analyzer. The ionization source ionizes molecules, while the mass analyzer determines the mass-to-charge ratio (m/z) of ions.

New rapid and direct methods to help better understand the crude oil composition and properties from the analysis of whole crude oil will save producers, marketers, refiners and/or other crude oil users substantial expense, effort and time. Therefore, a need exists for an improved system and method for determining indicative properties of crude oil fractions from different sources.

SUMMARY

Systems and methods for determining the indicative properties of a hydrocarbon sample or a fraction of a hydrocarbon sample are provided. In accordance with the invention, indicative properties (i.e., cetane number, pour point, cloud point and aniline point of gas oil fraction; octane number of gasoline or naphtha fraction; and aromaticity of whole crude oils) are predicted by density and TOF-MS measurements of crude oils. The properties regarding the fractions of the crude oil, for example the gas oil and naphtha fractions of the crude oil, are provided without fractionation/distillation (crude oil assays) and will help producers, refiners, and marketers to benchmark the oil quality and, as a result, valuate the oils without performing the customary extensive and time-consuming crude oil assays.

BRIEF DESCRIPTION OF THE DRAWINGS

The process of the disclosure will be described in more detail below and with reference to the attached drawings in which the same number is used for the same or similar elements, and where.

DETAILED DESCRIPTION

A system and method is provided for determining one or more indicative properties of a hydrocarbon sample. Indicative properties (e.g., one or more of cetane number, pour point, cloud point and aniline point) of a gas oil fraction in crude oil samples are assigned as a function of TOF-MS measurements of a crude oil sample and the density of the crude oil sample.

The correlations provide information about gas oil and/or naphtha indicative properties without fractionation/distillation (crude oil assays) and will help producers, refiners, and marketers to benchmark the oil quality and, as a result, valuate the oils without performing the customary extensive and time-consuming crude oil assays. The currently used crude oil assay method is costly in terms of money and time. It costs more than about $50,000 US and takes two months to complete one assay. With the method and system herein, the crude oil can be classified as a function of TOF-MS measurement data, and thus decisions can be made for purchasing and/or processing.

The systems and methods are applicable for naturally occurring hydrocarbons derived from crude oils, bitumens, heavy oils, shale oils and from refinery process units including hydrotreating, hydroprocessing, fluid catalytic cracking, coking, and visbreaking or coal liquefaction. Samples can be obtained from various sources, including an oil well, stabilizer, extractor, or distillation tower.

TOF-MS is a mass spectrometric method that is based on the principle that ions with the same energy but different masses travel with different velocities. The mass-to-charge ratio (m/z) is determined by the time an ion takes to arrive at the detector. Ions formed are accelerated by an electrostatic field over a distance to the detector, where the lighter ions arrive earlier in time than the heavier ions, since the velocity of the ions is dependent on their m/z ratio. The mass of each ion can be determined by measuring the flight time of the ion. A mass spectrum is recorded as a signal from the detector.

Figure 1A:
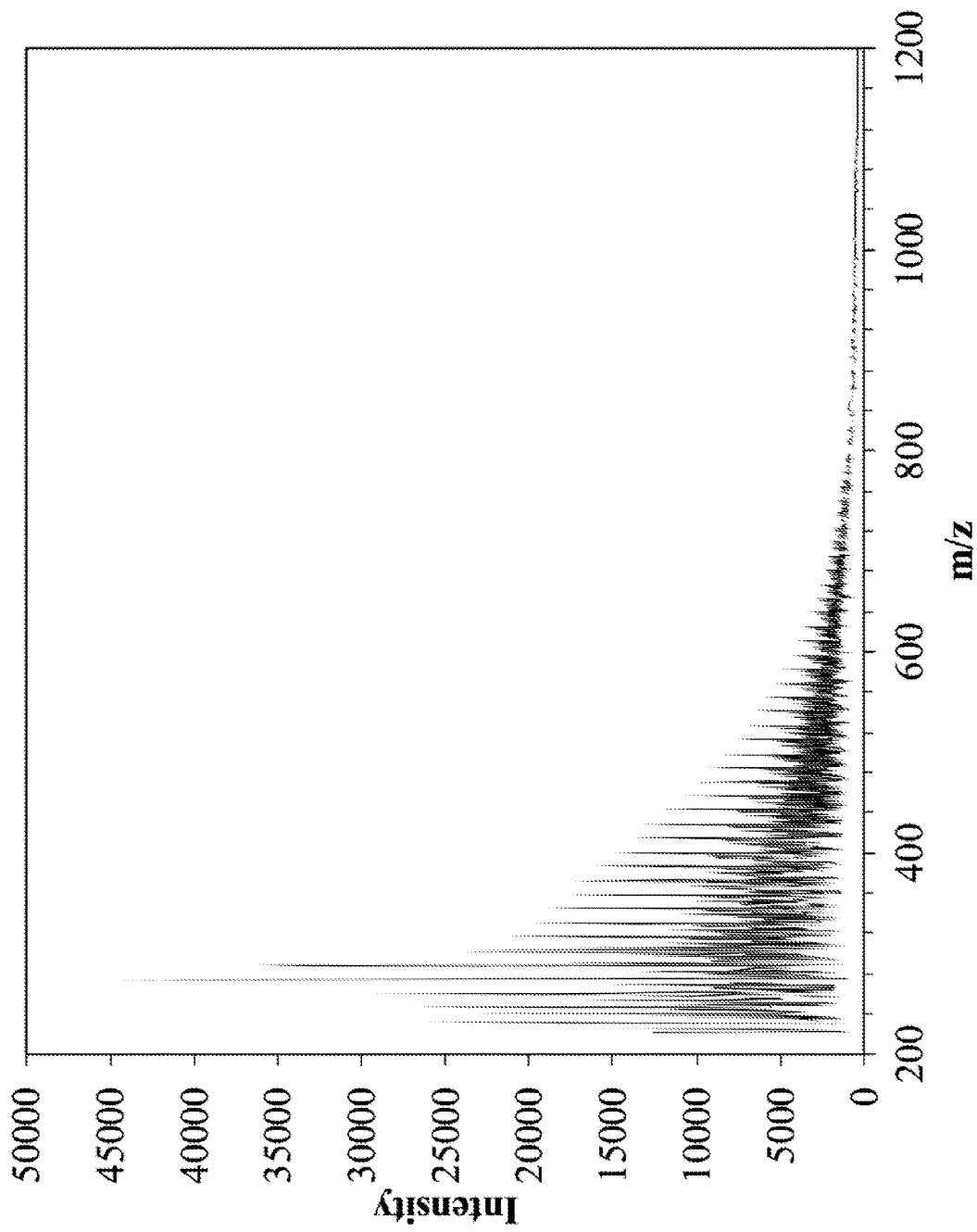
FIG. 1a is a graphic plot of typical TOF-MS data for a crude oil sample solution prepared as described below.

In the system and method herein, a mass spectra is obtained by a suitable known or to be developed TOF-MS instruments, and from this spectra signal intensity data is obtained (for example, Y-axis in FIG. 1a, which shows the TOF-MS data for a sample with an API Gravity of 28.8°) as a function of the m/z of ions (X-axis in FIG. 1a).

In certain embodiments, the TOF-MS data can be over a mass-to-charge ratio range of 220-3000 m/z.

The m/z raw data, i.e., the TOF-MS data, can be converted to show the cumulative mass fraction, or spectral abundance, of each m/z value. In other words, the TOF-MS data is representative of cumulative mass fraction data. In general, in order to convert to cumulative mass fraction for each m/z/ value, the intensity for the second m/z value in the original TOF-MS data set is added to the intensity of the first m/z value; the intensity for the third m/z value is added to the sum of the first two m/z values, and so on. Those cumulative values are normalized by dividing by the sum of all the peaks in the original TOF-MS data set. Examples of the cumulative mass fraction data for API Gravity 28.8°, is shown in Table 3. For example, a cumulative mass fraction of 0.20 corresponds to the mass value at the 20% percentile of total peak intensity in the original TOF-MS data set.

TABLE 3

| API Gravity = 28.8° | |
| --- | --- |
| Cumulative Mass Fraction | Mass (amu) |
| 0.00 | 213 |
| 0.05 | 239 |
| 0.10 | 259 |
| 0.20 | 287 |
| 0.30 | 317 |
| 0.40 | 357 |
| 0.50 | 396 |

TABLE 3-continued

| API Gravity = 28.8° | |
| --- | --- |
| Cumulative Mass Fraction | Mass (amu) |
| 0.60 | 442 |
| 0.70 | 498 |
| 0.80 | 570 |
| 0.90 | 681 |
| 0.95 | 790 |
| 1.00 | 1209 |

Figure 1B:
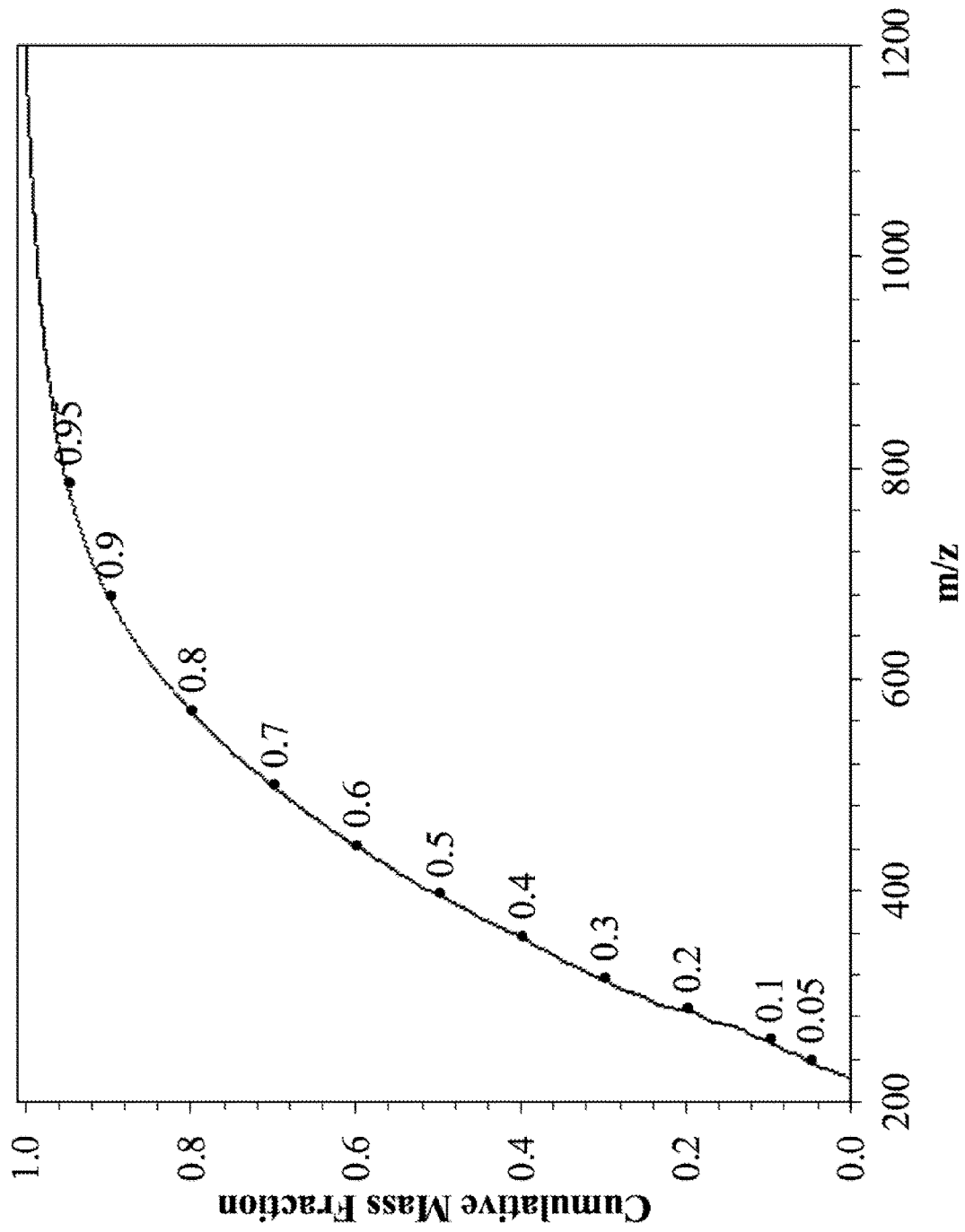
FIG. 1b is a graphic plot of the cumulative mass fraction of the TOF-MS data for a crude oil sample solution prepared as described below.
Figure 1C:
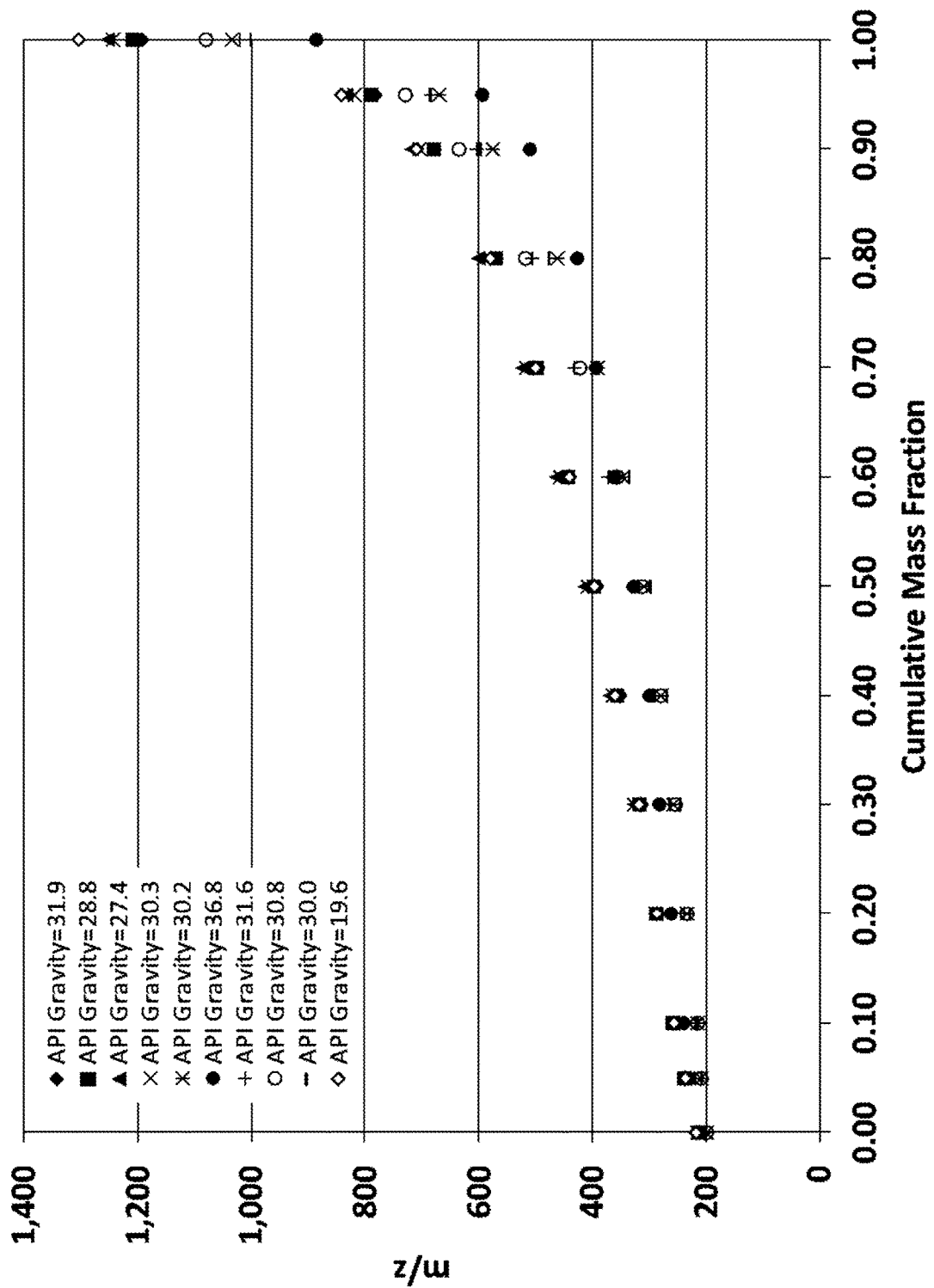
FIG. 1c is a graphic plot of the cumulative mass fraction of the TOF-MS data for a number of crude oil samples.

The m/z ratio vs. cumulative mass fraction for a sample with an API Gravity of 28.8° is shown in FIG. 1b. The cumulative mass fraction for a number of crude oil samples is shown in FIG. 1c.

Under typical operating conditions for petroleum samples, singly charged ions are generated. One can thus interpret that m/z values from the TOF-MS are also the mass (m) values in atomic mass units (amu).

TOF-MS includes two main components: an ionization source and a mass analyzer. The ionization source ionizes molecules, while the mass analyzer determines the mass-to-charge ratio (m/z) of ions.

A number of ionization sources have been used in TOF-MS, with some being preferable for gases, others for liquids, and others for solids. Ionization sources for TOF-MS include electron ionization (EI), which uses a glowing filament, which may break down the molecules under study. Inductively coupled plasma ionization (ICP) is a destructive technique which applies heat to reduce a sample to its atomic components. Chemical ionization (CI), a subset of EI, adds gases such as methane, isobutane, or ammonia, producing results that are less damaging to the molecules under study. Direct analysis in real time (DART) ionizes samples at atmospheric pressure using an electron beam. Matrix-assisted, laser desorption ionization (MALDI) is a solid phase process that uses laser energy to ionize molecules off a metal target plate. Electrospray ionization (ESI), is a liquid phase process that produces a fine mist of charged droplets that are dried in a countercurrent movement of heated gas to produce charge analytes in the gas phase. Field desorption/field ionization (FD/FI) relies on doping the sample onto and emitter, and then combines the processes of ionization and subsequent desorption of the ions formed on the surface of a field emitter into the mass spectrometer.

TOF-MS of petroleum samples frequently relies on atmospheric pressure photoionization (APPI), which uses a photon discharge from high-intensity ultraviolet light to ionize the solvent gas, which in turn ionizes the sample molecules. APPI works well with highly non-polar aromatic molecules like alkyl substituted benzenes, naphthalenes and anthracenes, and FD/FI works well with paraffinic or naphthenic molecules as well as aromatic molecules.

Thus, for the purpose of petroleum characterization, TOF-MS is conducted using preferably APPI or FD/FI. For APPI operation, a petroleum sample is diluted in an appropriate solvent such as toluene, and infused into the spectrometer. The diluted sample is delivered via syringe pump directly into the APPI source. For FD/FI operation, the diluted sample is adsorbed via syringe onto a FD/FI emitter mounted on a FD probe. Immediately after the probe is transferred into the ion source of the TOF MS the analysis is started by ramping the emitter current to desorb the sample.

Figure 2:
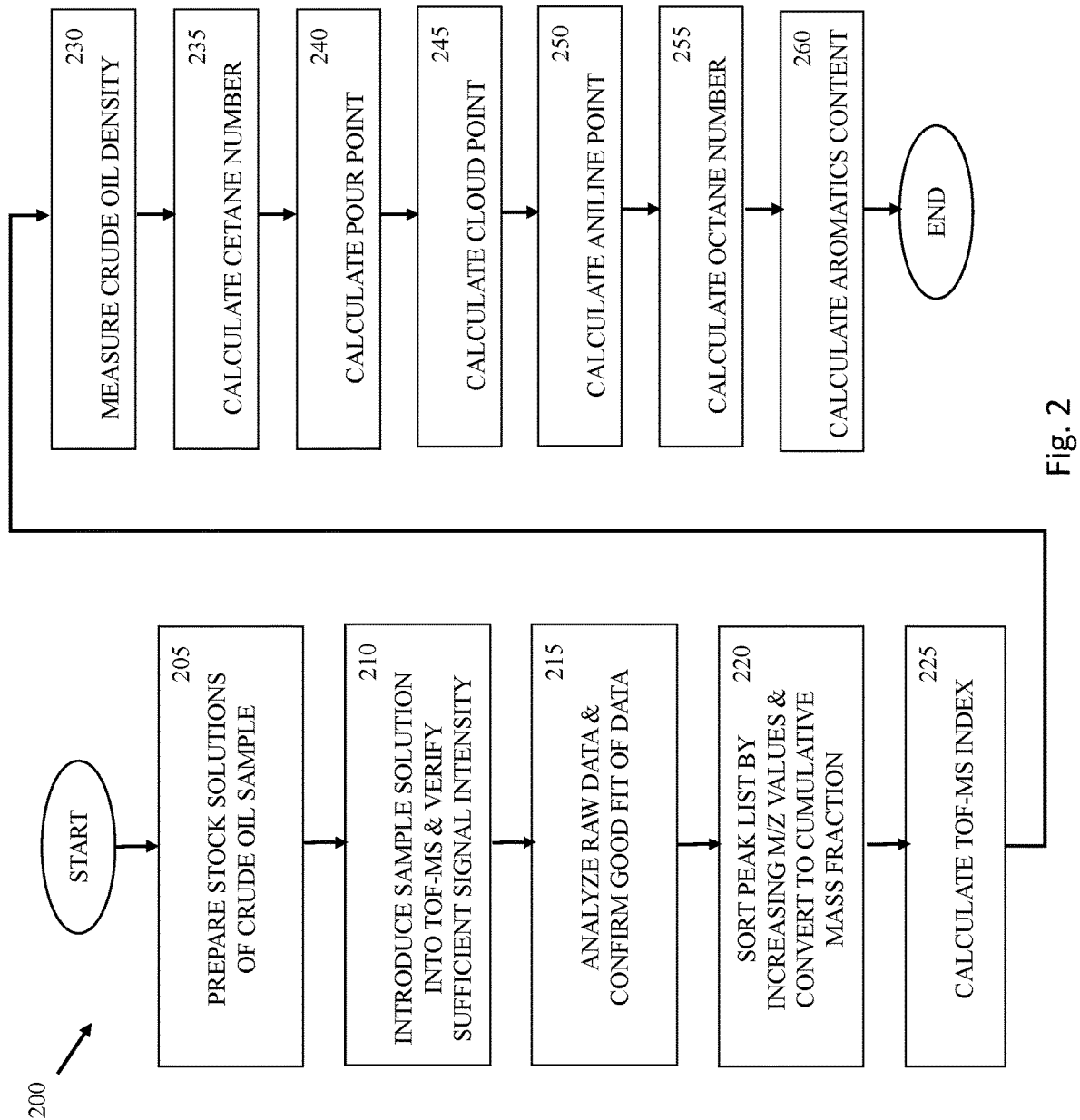
FIG. 2 is a block diagram of a method in which an embodiment herein is implemented.

FIG. 2 shows a process flowchart of a method 200 according to one embodiment herein. Solutions of crude oil samples are prepared, step 205. A prepared solution is infused into an TOF-MS, using atmospheric pressure photo ionization (APPI), or adsorbed onto a field desorption emitter for field desorption/field ionization (FD/FI), step 210. The raw data from step 210 is analyzed, peak picked and the baseline signal offset set to zero, step 215. At step 220, the data from step 215 is sorted by increasing m/z values and the data is converted to the cumulative mass fraction, or spectral abundance. In step 225, a Time of Flight Mass Spectrometry index (TOF-MSI, or TOFMSI) is calculated and assigned. In step 230, the density of the crude oil sample is measured. In steps 235, 240, 245, 250, 255, 260 the cetane number, the pour point, the cloud point, the aniline point, the octane number, and the aromatics content are each calculated. While FIG. 2 shows steps 235 through 260 performed sequentially, they can be performed in any order, and in certain embodiments fewer than all of the indicative properties can be calculated and assigned.

Equation (1) shows the TOFMSI which is calculated in step 225:

$$(TOF-MSI) = \frac{\left[\sum_{x,y=5,10,20,30,40,50,60,70,80,90,95} M_x * W_y\right]}{\left[\sum_{y=5,10,20,30,40,50,60,70,80,90,95} W_y\right]} \quad (1)$$

where:
M=mass
W=weight fraction of the mass, i.e., cumulative mass fraction.

The calculated TOFMSI for various crude oils are shown in Table 4.

TABLE 4

| °API Gravity | 31.9 | 28.8 | 27.4 | 30.3 | 30.2 | 36.8 | 31.6 | 30.8 | 30.0 | 19.6 |
|---|---|---|---|---|---|---|---|---|---|---|
| TOF-MSI | 536 | 539 | 566 | 557 | 421 | 442 | 466 | 476 | 445 | 555 |

The indicative properties (e.g., the cetane number, pour point, cloud point and aniline point of the gas oil fraction boiling in the range 180-370° C. and octane number for naphtha fraction boiling in the range 36-180° C.) of the fractions of crude oil can be predicted from the density of whole crude oil (which is determined in step 230), and from the TOFMSI of crude oil (which was determined in step 225). That is, $$\text{Indicative Property} = f(\text{density}_{Crude\ oil}, \text{TOFMSI}_{crude\ oil}) \quad (2);$$

Equations (3) through (6) show, respectively, the cetane number, pour point, cloud point aniline point of gas oils boiling in the range 180-370° C., and equation (7) shows the octane number of naphtha boiling in the range 36-180° C. that can be predicted from the density and TOF-MSI of crude oils. Thus, in step 235, the cetane number is calculated as:

$$\text{Cetane Number(CET)} = K_{CET} + X1_{CET}*DEN + X2_{CET}*DEN^2 + X3_{CET}*DEN^3 + X4_{CET}*TOFMSI + X5_{CET}*TOFMSI^2 + X6_{CET}*TOFMSI^3 + X7_{CET}*DEN*TOFMSI \quad (3)$$

In step 240, the pour point is calculated as:

$$\text{Pour Point(PPT)} = K_{PPT} + X1_{PPT}*DEN + X2_{PPT}*DEN^2 + X3_{PPT}*DEN^3 + X4_{PPT}*TOFMSI + X5_{PPT}*TOFMSI^2 + X6_{PPT}*TOFMSI^3 + X7_{PPT}*DEN*TOFMSI \quad (4)$$

In step 245, the cloud point is calculated as:

$$\text{Cloud Point(CPT)} = K_{CPT} + X1_{CPT}*DEN + X2_{CPT}*DEN^2 + X3_{CPT}*DEN^3 + X4_{CPT}*TOFMSI + X5_{CPT}*TOFMSI^2 + X6_{CPT}*TOFMSI^3 + X7_{CPT}*DEN*TOFMSI \quad (5)$$

In step 250, the aniline point is calculated as:

$$\text{Aniline Point(AP)} = K_{AP} + X1_{CPT}*DEN + X2_{AP}*DEN^2 + X3_{AP}*DEN^3 + X4_{AP}*TOFMSI + X5_{AP}*TOFMSI^2 + X6_{AP}^1*TOFMSI^3 + X7_{AP}*DEN*TOFMSI \quad (6)$$

In step 255, the octane number is calculated as:

$$\text{Octane Number(ON)} = K_{ON} + X1_{ON}*DEN + X2_{ON}*DEN^2 + X3_{ON}*DEN^3 + X4_{ON}*TOFMSI + X5_{ON}*TOFMSI^2 + X6_{ON}*TOFMSI^3 + X7_{ON}*DEN*TOFMSI \quad (7)$$

In step 260, the aromatics content of the crude oil sample is calculated as:

$$\text{Aromatics(AROM)} = K_{AROM} + X1_{AROM}*DEN + X2_{AROM}*DEN^2 + X3_{AROM}*DEN^3 + X4_{AROM}*TOFMSI + X5_{AROM}*TOFMSI^2 + X6_{AROM}*TOFMSI^3 + X7_{AROM}*DEN*TOFMSI \quad (8)$$

where:
DEN=density of the crude oil sample;
TOFMSI=Time of flight mass spectrometry index (derived from TOF-MS data); and
$K_{CET}$, $X1_{CET}$-$X7_{CET}$, $K_{PPT}$, $X1_{PPT}$-$X7_{PPT}$, $K_{CPT}$, $X1_{CPT}$-$X7_{CPT}$, $K_{AP}$, $X1_{AP}$-$X7_{AP}$, $K_{ON}$, $X1_{ON}$-$X7_{ON}$, $K_{AROM}$, $X1_{AROM}$-$X7_{AROM}$ are constants that were developed using linear regression analysis of hydrocarbon data from the APPI mode of TOF-MS.

Figure 3:
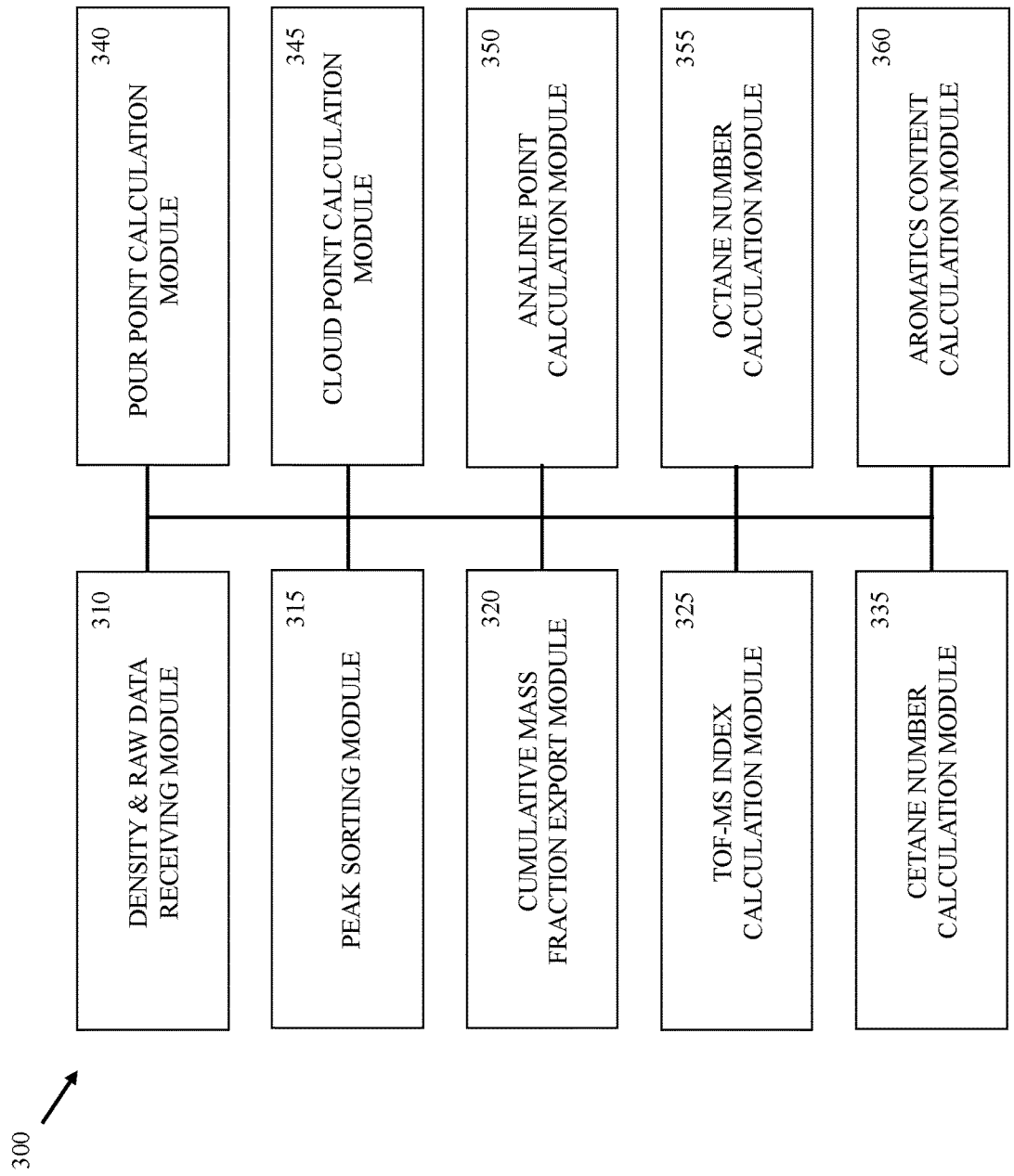
FIG. 3 is a schematic block diagram of modules of an embodiment of herein.

FIG. 3 illustrates a schematic block diagram of modules in accordance with an embodiment of the present invention, system 300. Density and raw data receiving module 310 receives TOF-MS data derived from the corresponding crude oil and the density of a sample of crude oil. Peak sorting module 315 sorts the peaks by increasing m/z values. Cumulative mass fraction export module 320 uses the data to calculate the cumulative mass fraction of the gas oil fraction. Module 325 calculates the TOFMSI. Cetane number calculation module 335 derives the cetane number for the gas oil fraction as a function of the density of the sample and the cumulative mass fraction, which is derived from the TOF-MS peak intensity of the sample. Pour point calculation module 340 derives the pour point for the gas oil fraction as a function of the density of the sample and the cumulative mass fraction, which is derived from the TOF-MS peak intensity of the sample. Cloud point calculation module 345 derives the cloud point for the gas oil fraction as a function of the density of the sample and the cumulative mass fraction, which is derived from the TOF-MS peak intensity of the sample. Aniline point calculation module 350 derives the aniline point for the gas oil fraction as a function of the density of the sample and the cumulative mass fraction, which is derived from the TOF-MS peak intensity of the sample. Octane number calculation module 355 derives the octane number for the naphtha fraction as a function of the density of the sample and the cumulative mass fraction, which is derived from the TOF-MS peak intensity of the sample. Aromatic content calculation module 360 derives the aromatic content for the crude oil sample as a function of the density of the sample and the cumulative mass fraction, which is derived from the TOF-MS peak intensity of the sample.

Figure 4:
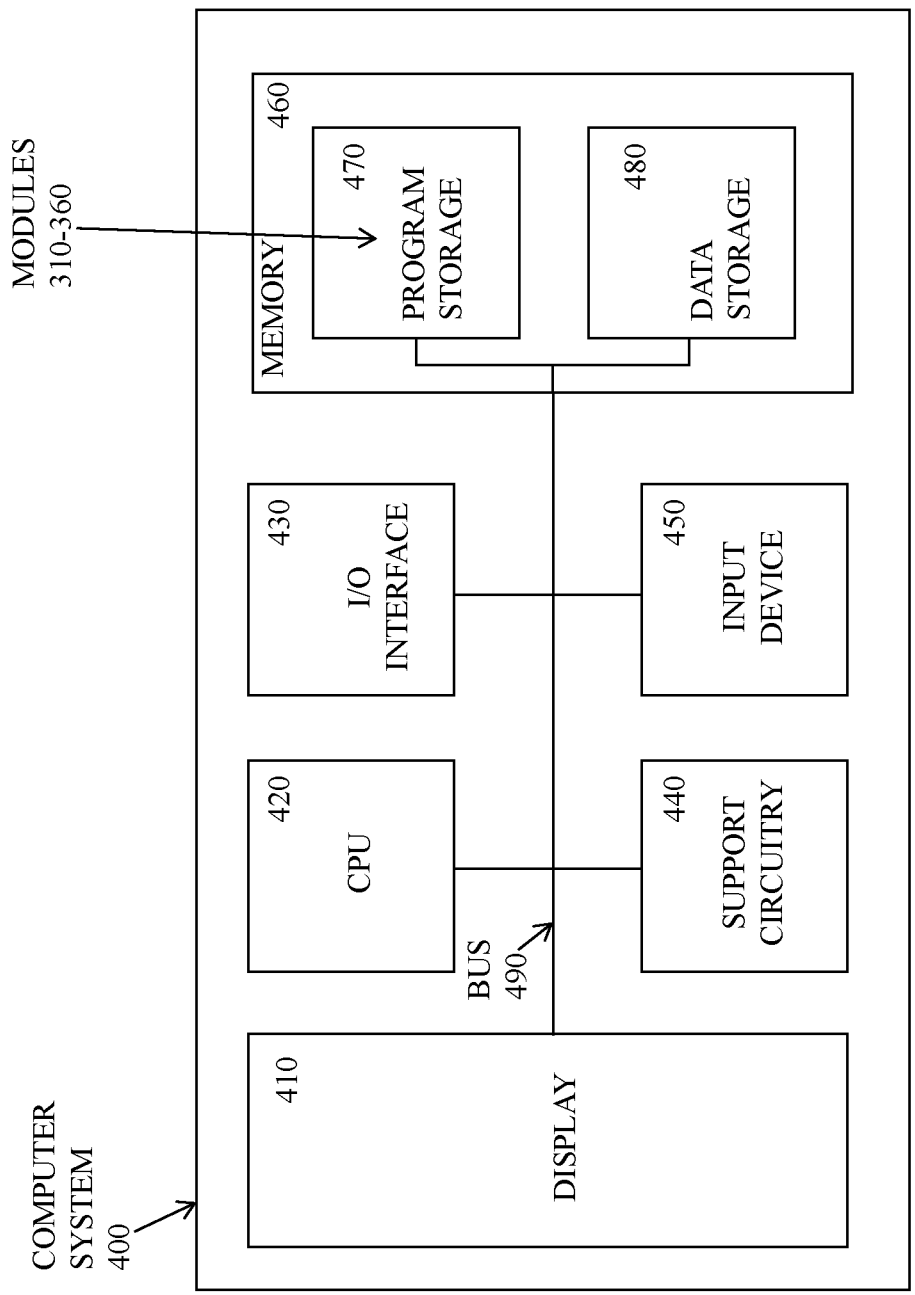
FIG. 4 is a block diagram of a computer system in which an embodiment herein is implemented.

FIG. 4 shows an exemplary block diagram of a computer system 400 by which the herein calculation modules can be implemented is shown in FIG. 4. Computer system 400 includes a processor 420, such as a central processing unit, an input/output interface 430 and support circuitry 440. In certain embodiments, where the computer system 400 requires a direct human interface, a display 410 and an input device 450 such as a keyboard, mouse or pointer are also provided. The display 410, input device 450, processor 420, and support circuitry 440 are shown connected to a bus 490 which also connects to a memory 460. Memory 460 includes program storage memory 470 and data storage memory 480. Note that while computer system 400 is depicted with direct human interface components display 410 and input device 450, programming of modules and exportation of data can alternatively be accomplished over the input/output interface 430, for instance, where the computer system 400 is connected to a network and the programming and display operations occur on another associated computer, or via a detachable input device as is known with respect to interfacing programmable logic controllers.

Program storage memory 470 and data storage memory 480 can each comprise volatile (RAM) and non-volatile (ROM) memory units and can also comprise hard disk and backup storage capacity, and both program storage memory 470 and data storage memory 480 can be embodied in a single memory device or separated in plural memory devices. Program storage memory 470 stores software program modules and associated data, and in particular stores a density and raw data receiving module 310, peak sorting module 315, cumulative mass fraction export module 320, TOFMSI calculation module 325, cetane number calculation module 330, pour point calculation module 340, cloud point calculation module 345, aniline point calculation module 350, octane number calculation module 355, and aromatics content calculation module 360. Data storage memory 480 stores data used and/or generated by the one or more modules of the present invention, including but not limited to density of the crude oil sample, raw data generated by the TOF-MS with APPI or FD/FI source, and m/z correlations with cumulative mass fraction data.

The calculated and assigned results in accordance with the systems and methods herein are displayed, audibly outputted, printed, and/or stored to memory for use as described herein.

It is to be appreciated that the computer system 400 can be any general or special purpose computer such as a personal computer, minicomputer, workstation, mainframe, a dedicated controller such as a programmable logic controller, or a combination thereof. While the computer system 400 is shown, for illustration purposes, as a single computer unit, the system can comprise a group/farm of computers which can be scaled depending on the processing load and database size, e.g., the total number of samples that are processed and results maintained on the system. The computer system 400 can serve as a common multi-tasking computer.

Computer system 400 preferably supports an operating system, for example stored in program storage memory 470 and executed by the processor 420 from volatile memory. According to the present system and method, the operating system contains instructions for interfacing the device 400 to the calculation module(s). According to an embodiment of the invention, the operating system contains instructions for interfacing computer system 400 to the Internet and/or to private networks.

EXAMPLE

Crude oil samples were prepared and analyzed by atmospheric pressure photo ionization (APPI) TOF-MS according to the method 200 described herein, and illustrated in FIG. 2.

In step 205, stock solutions of crude oil samples were prepared by homogenizing for 20 s on the Vortexer mixer at 2000 rpm. The homogenized sample was then diluted in analytical grade toluene to a concentration of 0.10 mg/g. A mass spectra of each sample was acquired on a 6230 TOF mass spectrometer (Agilent Technologies), or equivalent, equipped with atmospheric pressure photo ionization (APPI) source.

Key Instrument Parameters

For each analysis of a sample, the operator tuned the spectrometer settings to optimize performance. Key parameters and default settings follow:

Solvent: toluene
Sample dilution: 1:1,000 to 1:100,000
Flow rate: 10 µL/min to 40 µL/min
Nebulizer gas ($N_2$) flow: 2 mL/min to 5 mL/min
Average Spectra: 60
Source Accumulation: 1 Hz
APPI Temperature 300-450° C., depending on sample
Skimmer 1 potential: 25 V to 65 V
Ion extraction potential: 140 V to 250 V
Low Mass: 90 to 220 m/z (amu)
High Mass: 3000 m/z (amu)

Analysis

In step 210, the diluted sample was delivered via a syringe pump at a flow rate of 20 µL/min directly into the APPI source. A stable ionizer spray is essential and was maintained for all samples. Gas flow rates (nebulizer and dry gas) were set to 8 L/min and 40 psig, respectively. The APPI furnace temperature was set to 400° C. and the drying gas temperature to 325° C. Ion source potentials were set as follows: Capillary: 3.0 kV, Capillary end cap (fragmentor) and skimmer are set to 150 V and 65 V, respectively. Mass spectra were recorded from 90-3000 amu for one minute at a rate of 1 Hz and the resulting 60 spectra were co-added to improve the signal to noise ratio. The spectra shown in FIG. 1a has been truncated to show the range of from 222 to 1210 amu, which corresponds to the range of masses where relevant species for this particular sample occur.

The operator checked the signal shape at the beginning, middle and end of the mass range. An excessive sample load can be diagnosed by a signal cutoff through detector saturation. In case of signal cutoff, the signal will rise and abruptly plateau before descending to the baseline. When the operator observes such signal saturation, the sample should be diluted until a good signal shape is obtained.

Data Processing Workflow

In step 215, data processing was performed with the instrument control software for peak picking, to export a mass list of the peaks with at least 3 times intensity above baseline noise. The signal baseline must be set to zero before exporting the peak list, or the baseline offset from zero must be subtracted from the data in the following processing step. A list of m/z values and intensities are stored, for example as a text file or a comma separated value file (csv).

In step 220, the peak list was sorted according to increasing m/z values using a spreadsheet calculation software, for instance Microsoft Excel, and the relative cumulative abundance is summed from low to high m/z values.

Exemplary constants $K_{CET}$, $X1_{CET}$-$X7_{CET}$, $K_{PPT}$, $X1_{PPT}$-$X7_{PPT}$, $K_{CPT}$, $X1_{CPT}$-$X7_{CPT}$, $K_{AP}$, $X1_{AP}$-$X7_{AP}$, $K_{ON}$, $X1_{ON}$-$X7_{ON}$, $K_{AROM}$, $X1_{AROM}$-$X7_{AROM}$ were developed using linear regression analysis of hydrocarbon data from the APPI mode of TOF-MS, and are given in Tables 5.

TABLE 5

| Constants | Cetane Number | Pour point | Cloud Point | Aniline Point | Octane Number | Aromatics |
|---|---|---|---|---|---|---|
| K | 2.20E+05 | −1.33E+04 | 5.62E+04 | 1.06E+05 | 1.74E+05 | 1.03E+05 |
| $X_1$ | −7.52E+05 | 5.15E+04 | −1.92E+05 | −3.65E+05 | −6.07E+05 | −3.51E+05 |
| $X_2$ | 8.50E+05 | −4.94E+04 | 2.20E+05 | 4.12E+05 | 7.04E+05 | 3.96E+05 |
| $X_3$ | −3.19E+05 | 1.26E+04 | −8.42E+04 | −1.54E+05 | −2.73E+05 | −1.48E+05 |
| $X_4$ | 1.14E+01 | −2.58E+01 | −3.39E+00 | 1.23E+01 | 2.78E+00 | 4.92E+00 |
| $X_5$ | −1.37E−02 | 3.32E−02 | 6.33E−03 | −2.00E−02 | −9.85E−03 | −2.34E−03 |
| $X_6$ | 7.78E−06 | −2.32E−05 | −4.40E−06 | 1.31E−05 | 6.76E−06 | 1.58E−06 |
| $X_7$ | −3.97E+00 | 1.16E+01 | 4.38E−01 | −2.52E+00 | 2.18E+00 | −4.33E+00 |

A sample of Arabian medium crude with a 15° C./4° C. density of 0.8828 Kg/l was analyzed by TOF-MS, using the described method. The mass spectral data is depicted in FIG. 1a and listed in Table 6, with intensity in arbitrary units, for the sample with an API gravity of 28.8°.

The cumulative mass fraction was calculated with representative data presented in Table 3. The TOFMSI was calculated using equation (1) by taking the weighted average of the masses, with the value in the example calculated as 539. The application of equations (3) through (8) and the constants from Table 5 are shown in Tables 7a-7f.

In alternate embodiments, the present invention can be implemented as a computer program product for use with a computerized computing system. Those skilled in the art will readily appreciate that programs defining the functions of the present invention can be written in any appropriate programming language and delivered to a computer in any form, including but not limited to: (a) information permanently stored on non-writeable storage media (e.g., read-only memory devices such as ROMs or CD-ROM disks); (b) information alterably stored on writeable storage media (e.g., floppy disks and hard drives); and/or (c) information conveyed to a computer through communication media, such as a local area network, a telephone network, or a public network such as the Internet. When carrying computer readable instructions that implement the present invention methods, such computer readable media represent alternate embodiments of the present invention.

As generally illustrated herein, the system embodiments can incorporate a variety of computer readable media that comprise a computer usable medium having computer readable code means embodied therein. One skilled in the art will recognize that the software associated with the various processes described can be embodied in a wide variety of computer accessible media from which the software is loaded and activated. Pursuant to In re Beauregard, 35 USPQ2d 1383 (U.S. Pat. No. 5,710,578), the present invention contemplates and includes this type of computer readable media within the scope of the invention. In certain embodiments, pursuant to In re Nuijten, 500 F.3d 1346 (Fed. Cir. 2007) (U.S. patent application Ser. No. 09/211,928), the scope of the present claims is limited to computer readable media, wherein the media is both tangible and non-transitory.

The system and method of the present invention have been described above and with reference to the attached figure; however, modifications will be apparent to those of ordinary skill in the art and the scope of protection for the invention is to be defined by the claims that follow.

TABLE 6

| m/z | intensity | m/z | intensity | m/z | intensity | m/z | intensity | m/z | intensity |
|---|---|---|---|---|---|---|---|---|---|
| 222.13 | 12594.72 | 389.21 | 2641.83 | 519.48 | 2103.23 | 654.61 | 1906.62 | 833.88 | 471.38 |
| 222.22 | 2067.73 | 389.31 | 3386.20 | 520.22 | 1213.26 | 654.69 | 734.25 | 834.65 | 901.47 |
| 223.13 | 6722.25 | 389.40 | 1235.93 | 520.31 | 2689.64 | 655.50 | 1394.48 | 834.80 | 889.57 |
| 223.18 | 1374.41 | 390.14 | 1918.44 | 520.40 | 4903.98 | 655.61 | 1269.49 | 834.89 | 498.82 |
| 223.22 | 954.79 | 390.23 | 5341.49 | 520.49 | 3081.92 | 655.70 | 552.97 | 835.65 | 758.80 |
| 224.14 | 14547.53 | 390.32 | 5883.11 | 521.31 | 1720.84 | 656.43 | 1441.05 | 835.81 | 713.64 |
| 225.13 | 5673.74 | 390.40 | 1304.60 | 521.41 | 2843.13 | 656.53 | 2098.76 | 836.66 | 875.13 |
| 225.21 | 1512.83 | 391.27 | 5125.12 | 521.50 | 2062.90 | 656.62 | 1551.85 | 836.81 | 689.20 |
| 226.07 | 31717.96 | 391.32 | 3945.80 | 522.23 | 1226.64 | 657.51 | 1599.09 | 837.67 | 744.43 |
| 226.16 | 10691.33 | 392.16 | 3137.04 | 522.33 | 2398.10 | 657.63 | 1187.31 | 837.82 | 570.48 |
| 227.09 | 12541.23 | 392.24 | 6864.03 | 522.42 | 4026.65 | 658.45 | 1637.37 | 838.67 | 907.27 |
| 227.16 | 5868.17 | 392.33 | 6426.65 | 522.51 | 3145.28 | 658.55 | 2276.35 | 838.83 | 609.90 |
| 228.08 | 9247.86 | 393.24 | 4263.80 | 523.33 | 1677.00 | 658.64 | 1537.81 | 839.67 | 763.55 |
| 228.17 | 8828.18 | 393.33 | 10984.94 | 523.42 | 2478.23 | 659.45 | 1231.62 | 839.83 | 542.02 |
| 229.09 | 9175.74 | 394.18 | 5140.75 | 523.51 | 2139.11 | 659.56 | 1748.32 | 840.68 | 893.36 |
| 229.18 | 5013.60 | 394.26 | 8775.00 | 524.25 | 1412.51 | 659.64 | 1131.86 | 848.66 | 845.05 |
| 230.09 | 17045.89 | 394.34 | 8907.70 | 524.34 | 2758.73 | 660.46 | 1638.77 | 848.82 | 851.02 |
| 230.19 | 10274.82 | 395.18 | 3274.39 | 524.43 | 5212.75 | 660.56 | 2353.34 | 849.66 | 721.21 |
| 231.09 | 13631.51 | 395.26 | 4099.63 | 524.53 | 3685.11 | 660.65 | 1488.28 | 849.83 | 693.05 |
| 231.20 | 4844.13 | 395.35 | 4274.02 | 525.34 | 1885.34 | 661.53 | 1606.20 | 850.67 | 817.08 |
| 232.11 | 26292.05 | 396.18 | 4099.61 | 525.44 | 3081.02 | 661.65 | 1154.41 | 850.83 | 671.74 |
| 232.21 | 17891.34 | 396.27 | 5957.40 | 525.53 | 2150.46 | 662.47 | 1571.78 | 851.67 | 696.06 |
| 232.35 | 708.05 | 396.37 | 7824.90 | 526.27 | 1725.33 | 662.58 | 2141.67 | 851.84 | 533.82 |

TABLE 6-continued

| m/z | intensity | m/z | intensity | m/z | intensity | m/z | intensity | m/z | intensity |
|---|---|---|---|---|---|---|---|---|---|
| 233.11 | 8210.27 | 397.19 | 2533.10 | 526.36 | 3227.14 | 662.67 | 1559.80 | 852.68 | 841.62 |
| 233.21 | 5461.29 | 397.28 | 3300.88 | 526.45 | 7226.76 | 663.47 | 1215.09 | 852.84 | 581.03 |
| 234.12 | 12135.89 | 397.37 | 4416.75 | 526.54 | 3468.26 | 663.59 | 1598.10 | 853.68 | 710.00 |
| 234.22 | 2352.64 | 398.20 | 3879.09 | 527.27 | 1205.28 | 663.67 | 1152.27 | 853.85 | 490.30 |
| 235.08 | 4146.71 | 398.29 | 8594.89 | 527.36 | 2127.72 | 664.48 | 1720.34 | 854.69 | 873.58 |
| 235.13 | 5180.48 | 398.38 | 9575.85 | 527.45 | 3949.61 | 664.60 | 2441.94 | 854.86 | 551.42 |
| 235.19 | 1337.83 | 399.20 | 2459.81 | 527.54 | 1910.19 | 664.68 | 1570.85 | 855.69 | 720.08 |
| 235.23 | 1667.73 | 399.29 | 4230.07 | 528.28 | 1768.61 | 665.49 | 1306.17 | 855.87 | 487.22 |
| 236.06 | 3337.44 | 399.38 | 4473.25 | 528.37 | 3190.49 | 665.60 | 1688.47 | 856.70 | 856.06 |
| 236.14 | 10878.54 | 400.13 | 1757.47 | 528.46 | 3557.02 | 665.69 | 1057.74 | 856.88 | 527.40 |
| 236.23 | 1760.59 | 400.21 | 4423.38 | 528.55 | 1294.47 | 666.42 | 1241.12 | 857.70 | 697.48 |
| 237.07 | 2546.77 | 400.31 | 15000.70 | 529.29 | 1237.35 | 666.52 | 1835.18 | 857.88 | 485.86 |
| 237.15 | 5329.27 | 400.40 | 10634.80 | 529.38 | 2015.61 | 666.61 | 2684.50 | 858.70 | 795.85 |
| 237.21 | 1358.63 | 401.22 | 2661.98 | 529.47 | 2170.23 | 666.70 | 1368.94 | 858.89 | 530.49 |
| 238.07 | 3859.18 | 401.31 | 6262.05 | 529.56 | 773.06 | 667.50 | 1399.63 | 859.71 | 685.39 |
| 238.16 | 13164.57 | 401.40 | 4251.17 | 530.29 | 1886.82 | 667.62 | 1851.27 | 859.90 | 444.03 |
| 239.08 | 2153.27 | 402.14 | 2104.65 | 530.39 | 3476.10 | 667.70 | 923.15 | 860.71 | 815.94 |
| 239.16 | 5615.95 | 402.23 | 4466.56 | 530.48 | 2994.14 | 668.43 | 1294.66 | 860.91 | 506.41 |
| 239.22 | 1593.08 | 402.32 | 6475.96 | 530.56 | 820.03 | 668.53 | 1834.58 | 861.71 | 686.87 |
| 240.08 | 23465.11 | 402.40 | 2266.62 | 531.30 | 1364.18 | 668.62 | 1679.32 | 861.91 | 417.12 |
| 240.17 | 9497.20 | 403.23 | 2527.86 | 531.39 | 2367.44 | 668.71 | 706.53 | 862.68 | 841.15 |
| 241.09 | 6360.67 | 403.32 | 3312.50 | 531.48 | 1976.28 | 669.51 | 1352.04 | 862.83 | 776.96 |
| 241.18 | 5053.73 | 403.41 | 1196.81 | 532.31 | 2473.01 | 669.63 | 1215.57 | 862.92 | 432.89 |
| 242.09 | 4243.04 | 404.15 | 2074.00 | 532.40 | 4107.57 | 670.52 | 1996.75 | 863.72 | 676.56 |
| 242.19 | 8306.42 | 404.24 | 4752.47 | 532.49 | 2981.24 | 670.64 | 1430.78 | 864.69 | 812.25 |
| 243.10 | 3068.96 | 404.33 | 5191.02 | 533.31 | 1604.15 | 671.52 | 1462.71 | 864.85 | 613.27 |
| 243.19 | 4451.28 | 404.42 | 1294.19 | 533.41 | 2858.41 | 671.64 | 1123.81 | 865.69 | 693.51 |
| 244.11 | 11837.38 | 405.24 | 2801.74 | 533.50 | 1961.63 | 672.46 | 1572.62 | 865.85 | 522.41 |
| 244.21 | 10144.68 | 405.34 | 3115.77 | 534.32 | 2580.02 | 672.56 | 2114.25 | 866.70 | 808.82 |
| 245.12 | 7080.81 | 406.17 | 3015.39 | 534.42 | 4631.27 | 672.65 | 1417.12 | 866.86 | 530.67 |
| 245.21 | 4435.94 | 406.26 | 6423.27 | 534.51 | 2895.25 | 673.47 | 1195.74 | 867.70 | 700.63 |
| 246.13 | 27375.79 | 406.35 | 5518.67 | 535.33 | 1630.70 | 673.57 | 1614.80 | 867.86 | 475.46 |
| 246.22 | 18593.91 | 407.18 | 1853.90 | 535.42 | 2795.58 | 673.66 | 1087.18 | 868.70 | 817.97 |
| 247.13 | 9709.02 | 407.27 | 3972.99 | 535.51 | 1972.23 | 674.47 | 1607.32 | 868.88 | 549.72 |
| 247.23 | 5541.42 | 407.35 | 3301.16 | 536.25 | 1302.22 | 674.58 | 2209.88 | 869.71 | 679.89 |
| 248.06 | 5770.55 | 408.19 | 4260.92 | 536.34 | 2258.70 | 674.67 | 1434.18 | 869.89 | 473.18 |
| 248.14 | 11895.53 | 408.27 | 8248.34 | 536.43 | 3904.62 | 675.55 | 1529.36 | 870.71 | 764.98 |
| 248.23 | 2451.67 | 408.36 | 5604.98 | 536.52 | 3057.82 | 675.67 | 1020.12 | 870.89 | 514.46 |
| 249.06 | 2692.91 | 409.19 | 2542.01 | 537.34 | 1603.41 | 676.48 | 1452.43 | 871.71 | 695.67 |
| 249.14 | 5552.97 | 409.28 | 3973.14 | 537.44 | 2377.68 | 676.59 | 2064.10 | 871.90 | 455.79 |
| 249.24 | 1551.24 | 409.37 | 3365.79 | 537.53 | 2036.24 | 676.68 | 1425.25 | 872.71 | 763.19 |
| 250.07 | 4546.57 | 410.19 | 3590.52 | 538.27 | 1391.46 | 677.49 | 1174.00 | 872.91 | 491.69 |
| 250.16 | 10073.21 | 410.29 | 5636.69 | 538.36 | 2553.99 | 677.60 | 1464.31 | 873.72 | 673.56 |
| 250.25 | 1576.68 | 410.38 | 6449.09 | 538.45 | 4846.92 | 677.65 | 1037.65 | 873.91 | 431.88 |
| 251.08 | 2273.37 | 411.20 | 2378.73 | 538.54 | 3445.38 | 678.50 | 1632.35 | 874.72 | 760.25 |
| 251.16 | 5304.35 | 411.30 | 3163.98 | 539.35 | 1866.82 | 678.61 | 2331.96 | 874.93 | 496.12 |
| 252.09 | 6507.75 | 411.38 | 3851.05 | 539.46 | 2956.49 | 678.70 | 1439.83 | 875.73 | 658.86 |
| 252.17 | 10907.38 | 412.21 | 3771.62 | 539.54 | 1924.62 | 679.50 | 1223.55 | 876.73 | 761.78 |
| 253.09 | 2687.40 | 412.31 | 8070.67 | 540.28 | 1637.77 | 679.62 | 1602.24 | 876.93 | 423.47 |
| 253.18 | 6022.45 | 412.40 | 8651.16 | 540.37 | 3008.84 | 679.70 | 954.02 | 877.72 | 638.56 |
| 253.24 | 1565.15 | 413.21 | 2436.96 | 540.47 | 6471.93 | 680.51 | 1724.21 | 878.70 | 762.89 |
| 254.10 | 17629.49 | 413.31 | 4244.87 | 540.56 | 3252.38 | 680.63 | 2468.42 | 878.86 | 575.20 |
| 254.19 | 9420.12 | 413.40 | 4154.93 | 541.29 | 1190.91 | 680.71 | 1226.72 | 879.70 | 657.37 |
| 255.11 | 5149.57 | 414.22 | 4307.31 | 541.38 | 2038.76 | 681.51 | 1283.09 | 879.86 | 482.86 |
| 255.19 | 4839.92 | 414.32 | 13796.98 | 541.47 | 3584.17 | 681.63 | 1681.55 | 880.71 | 773.74 |
| 256.11 | 5263.88 | 414.41 | 9390.41 | 541.56 | 1778.75 | 681.72 | 842.94 | 880.88 | 524.51 |
| 256.21 | 8019.13 | 415.23 | 2689.44 | 542.30 | 1728.64 | 682.45 | 1264.96 | 881.71 | 654.97 |
| 257.02 | 1335.83 | 415.33 | 6031.86 | 542.39 | 2972.59 | 682.55 | 1706.91 | 881.89 | 430.34 |
| 257.12 | 2953.52 | 415.42 | 3909.09 | 542.48 | 3369.22 | 682.64 | 1607.37 | 882.72 | 771.29 |
| 257.21 | 4257.14 | 416.16 | 2159.98 | 542.56 | 1194.60 | 682.73 | 674.27 | 882.89 | 490.96 |
| 258.03 | 1776.04 | 416.24 | 4218.59 | 543.30 | 1227.15 | 683.52 | 1259.02 | 883.72 | 672.23 |
| 258.13 | 14287.29 | 416.33 | 6106.44 | 543.39 | 1967.96 | 683.65 | 1128.61 | 883.90 | 440.21 |
| 258.22 | 10436.05 | 416.42 | 2093.63 | 543.48 | 2056.95 | 684.46 | 1364.57 | 884.72 | 770.00 |
| 259.13 | 7666.81 | 417.16 | 1303.66 | 543.57 | 749.75 | 684.56 | 1826.55 | 884.91 | 499.33 |
| 259.22 | 4470.90 | 417.25 | 2432.00 | 544.31 | 1899.71 | 684.65 | 1350.84 | 885.71 | 655.38 |
| 260.15 | 29734.39 | 417.34 | 3224.99 | 544.40 | 3363.96 | 685.54 | 1411.85 | 885.92 | 411.47 |
| 260.24 | 17868.81 | 417.43 | 1168.96 | 544.49 | 2648.35 | 685.66 | 1069.62 | 886.72 | 717.26 |
| 261.15 | 10753.97 | 418.17 | 2163.64 | 544.58 | 756.54 | 686.47 | 1491.29 | 886.92 | 474.16 |
| 261.24 | 5670.09 | 418.26 | 4524.64 | 545.31 | 1387.80 | 686.58 | 1987.90 | 887.73 | 639.53 |
| 262.07 | 9223.79 | 418.35 | 4685.66 | 545.41 | 2308.24 | 686.67 | 1315.09 | 887.93 | 402.91 |
| 262.15 | 10458.51 | 418.44 | 1224.02 | 545.50 | 1866.38 | 687.48 | 1156.98 | 888.74 | 725.94 |
| 262.25 | 2635.51 | 419.18 | 1362.18 | 546.33 | 2342.67 | 687.59 | 1512.22 | 888.94 | 451.95 |
| 263.08 | 3838.26 | 419.32 | 3044.81 | 546.42 | 3955.69 | 687.67 | 963.41 | 889.73 | 631.57 |
| 263.14 | 6127.42 | 420.19 | 2889.05 | 546.51 | 2803.84 | 688.49 | 1486.88 | 889.94 | 397.68 |
| 263.26 | 1682.34 | 420.28 | 6055.69 | 547.33 | 1611.44 | 688.60 | 2043.32 | 890.74 | 737.69 |
| 264.09 | 5199.26 | 420.37 | 5060.69 | 547.43 | 2772.64 | 688.68 | 1285.76 | 890.96 | 401.60 |
| 264.17 | 9308.86 | 421.19 | 1775.39 | 547.51 | 1906.67 | 689.49 | 1183.78 | 891.74 | 636.45 |
| 264.22 | 1957.73 | 421.28 | 3809.15 | 548.25 | 1175.40 | 689.60 | 1405.55 | 892.74 | 749.72 |

TABLE 6-continued

| m/z | intensity | m/z | intensity | m/z | intensity | m/z | intensity | m/z | intensity |
|---|---|---|---|---|---|---|---|---|---|
| 264.27 | 1727.24 | 421.37 | 3064.16 | 548.34 | 2406.73 | 689.69 | 959.85 | 893.72 | 641.35 |
| 265.16 | 4631.41 | 422.20 | 3592.66 | 548.44 | 4253.53 | 690.50 | 1427.28 | 893.88 | 463.00 |
| 265.24 | 1377.61 | 422.29 | 7700.95 | 548.52 | 2745.83 | 690.61 | 1876.30 | 894.73 | 767.96 |
| 266.10 | 8908.71 | 422.38 | 5006.94 | 549.35 | 1632.09 | 690.70 | 1295.31 | 894.90 | 497.70 |
| 266.19 | 9060.47 | 423.20 | 2042.85 | 549.44 | 2585.73 | 691.57 | 1358.42 | 895.72 | 629.96 |
| 267.11 | 3534.32 | 423.30 | 3777.58 | 549.53 | 1834.33 | 691.70 | 1004.66 | 895.91 | 421.07 |
| 267.19 | 4846.04 | 423.39 | 3051.09 | 550.35 | 2203.21 | 692.51 | 1526.76 | 896.73 | 772.42 |
| 267.25 | 1628.42 | 424.21 | 2969.69 | 550.45 | 3652.23 | 692.63 | 2096.25 | 896.91 | 470.08 |
| 268.03 | 1781.74 | 424.30 | 5406.49 | 550.54 | 2919.13 | 692.71 | 1341.38 | 897.73 | 632.15 |
| 268.12 | 15125.16 | 424.40 | 5587.71 | 551.36 | 1598.44 | 693.51 | 1155.20 | 897.92 | 420.45 |
| 268.21 | 8658.54 | 425.22 | 1957.35 | 551.46 | 2270.26 | 693.63 | 1502.44 | 898.74 | 719.75 |
| 269.12 | 4809.15 | 425.31 | 3060.54 | 551.54 | 1926.18 | 693.72 | 929.92 | 898.93 | 669.26 |
| 269.21 | 4548.66 | 425.40 | 3388.50 | 552.28 | 1410.80 | 694.52 | 1614.48 | 899.73 | 636.60 |
| 270.13 | 8128.48 | 426.22 | 3419.09 | 552.37 | 2536.11 | 694.64 | 2255.44 | 899.93 | 413.35 |
| 270.22 | 7598.64 | 426.32 | 7730.05 | 552.47 | 4508.33 | 694.73 | 1161.17 | 900.74 | 684.30 |
| 271.14 | 6415.40 | 426.41 | 8242.83 | 552.56 | 3246.85 | 695.52 | 1187.96 | 900.94 | 460.63 |
| 271.23 | 4260.25 | 427.23 | 2240.66 | 553.37 | 1808.36 | 695.65 | 1514.12 | 901.74 | 594.47 |
| 272.14 | 42167.76 | 427.33 | 4023.91 | 553.47 | 2814.96 | 695.73 | 760.07 | 902.74 | 733.88 |
| 272.24 | 10923.86 | 427.42 | 3964.24 | 553.56 | 1891.11 | 696.46 | 1222.14 | 902.95 | 419.97 |
| 273.15 | 28090.26 | 428.16 | 1905.41 | 554.30 | 1652.27 | 696.57 | 1606.38 | 903.75 | 625.93 |
| 273.24 | 4842.61 | 428.24 | 4103.50 | 554.39 | 2950.88 | 696.65 | 1476.49 | 904.71 | 691.56 |
| 274.16 | 47325.55 | 428.34 | 13178.45 | 554.48 | 5987.28 | 696.74 | 644.57 | 904.89 | 634.38 |
| 274.25 | 17865.22 | 428.43 | 7925.32 | 554.57 | 2988.46 | 697.54 | 1231.95 | 905.75 | 600.58 |
| 274.35 | 988.00 | 429.24 | 2636.01 | 555.39 | 1991.99 | 697.66 | 1035.11 | 906.72 | 705.58 |
| 274.41 | 839.17 | 429.34 | 5852.83 | 555.49 | 3398.80 | 698.55 | 1726.15 | 906.90 | 553.84 |
| 275.16 | 21524.43 | 429.43 | 3410.81 | 555.57 | 1682.29 | 698.67 | 1192.24 | 907.74 | 580.88 |
| 275.26 | 6017.80 | 430.17 | 2090.61 | 556.31 | 1648.01 | 699.56 | 1309.48 | 908.73 | 723.78 |
| 276.09 | 11727.30 | 430.26 | 4134.74 | 556.40 | 2879.80 | 699.68 | 959.43 | 908.90 | 479.63 |
| 276.16 | 15379.39 | 430.35 | 5796.79 | 556.49 | 3028.39 | 700.49 | 1380.36 | 909.73 | 611.58 |
| 276.26 | 2832.06 | 430.44 | 1961.03 | 556.58 | 1130.42 | 700.60 | 1796.88 | 910.74 | 706.28 |
| 277.15 | 6781.36 | 431.18 | 1347.81 | 557.40 | 1943.28 | 700.68 | 1225.09 | 910.92 | 445.01 |
| 277.27 | 1656.98 | 431.26 | 2419.25 | 557.50 | 1870.53 | 701.56 | 1402.09 | 911.74 | 621.72 |
| 278.11 | 5464.47 | 431.35 | 3123.45 | 557.59 | 710.08 | 701.69 | 955.75 | 911.93 | 426.20 |
| 278.19 | 9111.45 | 431.44 | 1065.92 | 558.32 | 1878.20 | 702.50 | 1387.79 | 912.74 | 683.14 |
| 278.28 | 1953.43 | 432.18 | 2108.55 | 558.42 | 3054.90 | 702.61 | 1891.27 | 912.95 | 427.30 |
| 279.17 | 4464.40 | 432.28 | 4377.16 | 558.51 | 2580.52 | 702.70 | 1181.63 | 913.73 | 605.21 |
| 280.12 | 9751.06 | 432.37 | 4526.84 | 559.33 | 1336.94 | 703.51 | 1089.69 | 913.94 | 395.45 |
| 280.21 | 8327.66 | 432.46 | 1109.13 | 559.43 | 2130.38 | 703.62 | 1303.18 | 914.75 | 668.87 |
| 281.12 | 4237.05 | 433.19 | 1391.07 | 559.51 | 1748.69 | 703.71 | 902.42 | 914.95 | 428.78 |
| 281.21 | 4960.46 | 433.28 | 2701.16 | 560.34 | 2281.26 | 704.51 | 1390.95 | 915.75 | 588.46 |
| 281.27 | 1552.49 | 433.37 | 2846.04 | 560.44 | 3702.72 | 704.63 | 1755.77 | 916.75 | 678.50 |
| 282.04 | 2927.60 | 434.20 | 2843.37 | 560.53 | 2598.36 | 704.72 | 1198.05 | 916.98 | 403.46 |
| 282.13 | 13774.77 | 434.29 | 5694.77 | 561.34 | 1572.35 | 705.58 | 1282.64 | 917.75 | 583.58 |
| 282.22 | 8290.50 | 434.38 | 4739.22 | 561.44 | 2620.38 | 705.72 | 910.59 | 918.76 | 669.26 |
| 283.14 | 5049.51 | 435.21 | 1731.48 | 561.53 | 1823.21 | 706.52 | 1451.79 | 919.76 | 596.88 |
| 283.23 | 4269.05 | 435.30 | 3742.45 | 562.35 | 2265.05 | 706.64 | 1919.86 | 920.76 | 678.03 |
| 284.15 | 8255.06 | 435.39 | 2854.45 | 562.45 | 3999.50 | 706.73 | 1173.05 | 921.75 | 559.93 |
| 284.24 | 7505.66 | 436.13 | 1120.28 | 562.54 | 2555.48 | 707.53 | 1161.53 | 922.75 | 681.55 |
| 285.15 | 6414.26 | 436.22 | 3453.72 | 563.36 | 1595.75 | 707.65 | 1381.92 | 922.93 | 449.34 |
| 285.24 | 4178.61 | 436.31 | 7245.30 | 563.46 | 2473.16 | 707.74 | 883.27 | 923.74 | 581.27 |
| 286.16 | 34415.01 | 436.40 | 4684.01 | 563.55 | 1767.45 | 708.54 | 1520.95 | 923.93 | 404.13 |
| 286.25 | 10739.50 | 437.22 | 1911.07 | 564.28 | 1178.06 | 708.66 | 2037.19 | 924.75 | 708.50 |
| 287.16 | 15994.11 | 437.31 | 3689.22 | 564.38 | 2120.41 | 708.74 | 1042.78 | 924.94 | 423.99 |
| 287.26 | 4736.08 | 437.40 | 2929.62 | 564.47 | 3428.46 | 709.54 | 1161.14 | 925.75 | 595.76 |
| 288.14 | 36295.07 | 438.23 | 2739.12 | 564.56 | 2598.38 | 709.66 | 1438.69 | 925.96 | 392.27 |
| 288.17 | 31877.57 | 438.32 | 5249.22 | 565.37 | 1562.44 | 709.75 | 743.57 | 926.76 | 645.31 |
| 288.27 | 17135.64 | 438.41 | 5018.07 | 565.47 | 2243.76 | 710.55 | 1516.28 | 926.95 | 428.05 |
| 289.15 | 29316.52 | 439.24 | 1830.67 | 565.56 | 1803.43 | 710.67 | 1380.05 | 927.76 | 590.00 |
| 289.27 | 5840.69 | 439.33 | 3030.22 | 566.29 | 1352.55 | 710.75 | 601.74 | 928.76 | 683.56 |
| 290.01 | 1009.59 | 439.42 | 3156.72 | 566.39 | 2498.05 | 711.55 | 1155.63 | 928.98 | 401.18 |
| 290.14 | 23028.88 | 440.24 | 3300.16 | 566.48 | 4237.80 | 711.68 | 990.27 | 929.75 | 581.68 |
| 290.28 | 3061.58 | 440.34 | 7345.55 | 566.57 | 2903.78 | 712.56 | 1581.46 | 930.76 | 652.40 |
| 291.13 | 17877.70 | 440.43 | 7555.94 | 567.39 | 1755.39 | 712.68 | 1138.07 | 931.77 | 556.64 |
| 291.16 | 12368.68 | 441.25 | 2151.05 | 567.49 | 2633.72 | 713.57 | 1247.15 | 932.77 | 654.85 |
| 291.29 | 1906.99 | 441.34 | 4015.92 | 567.57 | 1765.75 | 713.69 | 929.35 | 933.77 | 558.06 |
| 292.13 | 9346.38 | 441.43 | 3547.76 | 568.31 | 1630.56 | 714.50 | 1329.02 | 934.75 | 670.57 |
| 292.20 | 8866.10 | 442.17 | 1870.78 | 568.41 | 2744.65 | 714.61 | 1692.83 | 934.93 | 485.39 |
| 292.30 | 2107.05 | 442.26 | 3924.95 | 568.50 | 5415.74 | 714.70 | 1127.35 | 935.76 | 563.68 |
| 293.13 | 4753.77 | 442.35 | 11991.67 | 568.59 | 2602.50 | 715.58 | 1334.00 | 936.75 | 663.68 |
| 293.21 | 4467.52 | 442.44 | 7025.92 | 569.32 | 1186.40 | 715.70 | 845.87 | 936.94 | 441.84 |
| 294.13 | 9742.86 | 443.18 | 1309.79 | 569.41 | 1915.48 | 716.51 | 1300.97 | 937.76 | 569.63 |
| 294.22 | 7907.30 | 443.27 | 2453.38 | 569.50 | 3104.42 | 716.63 | 1739.16 | 938.77 | 676.70 |
| 295.14 | 4633.24 | 443.36 | 5715.90 | 569.59 | 1506.89 | 716.72 | 1086.70 | 939.77 | 589.49 |
| 295.23 | 4157.24 | 443.45 | 3127.79 | 570.33 | 1656.09 | 717.59 | 1281.99 | 939.97 | 374.77 |
| 295.28 | 1400.96 | 444.19 | 2157.43 | 570.42 | 2822.51 | 717.72 | 842.30 | 940.76 | 638.42 |
| 296.06 | 3185.48 | 444.28 | 4020.75 | 570.51 | 2864.12 | 718.52 | 1253.06 | 940.97 | 414.44 |
| 296.15 | 12749.97 | 444.37 | 5374.21 | 570.60 | 1052.55 | 718.64 | 1599.59 | 941.77 | 555.00 |
| 296.24 | 7846.08 | 444.45 | 1776.21 | 571.33 | 1206.89 | 718.73 | 1093.39 | 942.77 | 619.52 |

TABLE 6-continued

| m/z | intensity | m/z | intensity | m/z | intensity | m/z | intensity | m/z | intensity |
|---|---|---|---|---|---|---|---|---|---|
| 297.15 | 5019.84 | 445.19 | 1376.78 | 571.43 | 1884.69 | 719.59 | 1175.87 | 943.77 | 549.64 |
| 297.24 | 4133.94 | 445.28 | 2294.73 | 571.51 | 1797.54 | 719.73 | 835.96 | 944.78 | 621.06 |
| 298.16 | 7342.39 | 445.37 | 2917.67 | 571.60 | 691.89 | 720.54 | 1364.24 | 945.01 | 379.71 |
| 298.25 | 7028.16 | 445.46 | 1013.11 | 572.34 | 1749.82 | 720.66 | 1758.66 | 945.78 | 537.65 |
| 299.16 | 4012.58 | 446.20 | 2144.61 | 572.44 | 3033.56 | 720.75 | 1099.46 | 946.76 | 655.66 |
| 299.26 | 3940.15 | 446.29 | 4293.80 | 572.53 | 2317.10 | 721.61 | 1287.98 | 946.93 | 573.47 |
| 300.09 | 3404.76 | 446.38 | 4351.58 | 573.35 | 1362.90 | 721.75 | 802.54 | 947.78 | 566.09 |
| 300.18 | 14581.21 | 446.47 | 1055.88 | 573.44 | 2078.73 | 722.48 | 1127.71 | 948.78 | 631.19 |
| 300.27 | 9996.18 | 447.21 | 1412.19 | 573.53 | 1711.88 | 722.58 | 1442.59 | 949.77 | 531.26 |
| 301.17 | 6853.01 | 447.30 | 2702.48 | 574.36 | 2241.75 | 722.68 | 1838.56 | 950.77 | 626.74 |
| 301.27 | 4405.73 | 447.39 | 2787.49 | 574.45 | 3452.34 | 722.76 | 945.34 | 950.96 | 430.50 |
| 302.18 | 24126.15 | 448.22 | 2825.25 | 574.54 | 2402.51 | 723.55 | 1130.07 | 951.78 | 569.30 |
| 302.28 | 15590.80 | 448.31 | 5591.10 | 575.36 | 1561.91 | 723.68 | 1325.52 | 952.78 | 640.64 |
| 302.44 | 695.30 | 448.40 | 4573.87 | 575.46 | 2466.03 | 723.77 | 667.72 | 952.97 | 398.40 |
| 303.17 | 11252.39 | 449.22 | 1703.99 | 575.55 | 1648.65 | 724.56 | 1424.35 | 953.78 | 586.97 |
| 303.29 | 5390.81 | 449.31 | 3682.72 | 576.37 | 2265.58 | 724.69 | 1254.52 | 954.79 | 636.49 |
| 304.13 | 23305.67 | 449.40 | 2843.46 | 576.47 | 3726.97 | 725.57 | 1132.42 | 955.78 | 559.41 |
| 304.20 | 9478.34 | 450.14 | 1180.90 | 576.56 | 2389.42 | 725.69 | 894.36 | 956.78 | 605.58 |
| 304.30 | 2834.38 | 450.23 | 3264.96 | 577.37 | 1504.44 | 726.57 | 1509.84 | 957.78 | 529.51 |
| 305.14 | 19135.06 | 450.32 | 6751.73 | 577.47 | 2321.41 | 726.70 | 1049.48 | 958.78 | 611.42 |
| 305.20 | 4848.42 | 450.41 | 4427.77 | 577.56 | 1615.18 | 727.58 | 1188.27 | 959.79 | 543.00 |
| 305.30 | 1725.81 | 451.24 | 1921.94 | 578.38 | 2050.16 | 727.71 | 841.68 | 960.79 | 614.51 |
| 306.13 | 12759.82 | 451.33 | 3541.55 | 578.48 | 3246.26 | 728.59 | 1597.15 | 961.79 | 543.55 |
| 306.22 | 7775.33 | 451.42 | 2722.58 | 578.57 | 2446.25 | 728.71 | 1043.85 | 962.77 | 616.48 |
| 306.31 | 1983.14 | 452.16 | 1202.41 | 579.39 | 1530.85 | 729.59 | 1249.63 | 962.96 | 438.02 |
| 307.14 | 7500.55 | 452.25 | 2737.52 | 579.49 | 2156.80 | 729.72 | 845.85 | 963.78 | 539.97 |
| 307.22 | 4077.93 | 452.34 | 5016.82 | 579.58 | 1649.82 | 730.53 | 1265.01 | 963.97 | 382.75 |
| 307.32 | 1042.19 | 452.43 | 4617.43 | 580.31 | 1300.28 | 730.64 | 1597.52 | 964.78 | 620.54 |
| 308.15 | 10020.42 | 453.25 | 1811.48 | 580.41 | 2302.62 | 730.73 | 991.32 | 964.97 | 411.80 |
| 308.24 | 7591.26 | 453.34 | 2968.42 | 580.50 | 4050.47 | 731.60 | 1134.14 | 965.78 | 547.21 |
| 309.15 | 5197.80 | 453.43 | 2894.02 | 580.59 | 2633.67 | 731.74 | 807.48 | 966.80 | 617.34 |
| 309.24 | 3993.91 | 454.17 | 1447.22 | 581.40 | 1746.99 | 732.61 | 1466.12 | 967.80 | 556.73 |
| 309.30 | 1390.22 | 454.26 | 3320.87 | 581.50 | 2548.62 | 732.75 | 1023.55 | 968.79 | 600.87 |
| 310.08 | 3319.31 | 454.35 | 7056.90 | 581.59 | 1631.54 | 733.61 | 1135.62 | 969.79 | 510.43 |
| 310.16 | 12001.55 | 454.45 | 6591.69 | 582.33 | 1590.37 | 733.75 | 795.73 | 970.80 | 589.54 |
| 310.25 | 7447.27 | 455.26 | 2221.00 | 582.42 | 2540.57 | 734.55 | 1260.04 | 971.79 | 513.21 |
| 311.17 | 4985.10 | 455.36 | 3805.17 | 582.52 | 4953.29 | 734.68 | 1635.70 | 972.80 | 593.96 |
| 311.26 | 3963.49 | 455.45 | 3296.28 | 582.60 | 2384.76 | 734.76 | 1014.48 | 973.80 | 532.82 |
| 312.09 | 2502.28 | 456.19 | 1887.29 | 583.41 | 1813.99 | 735.56 | 1031.47 | 974.77 | 617.90 |
| 312.18 | 6669.38 | 456.28 | 3926.86 | 583.52 | 2933.81 | 735.68 | 1233.96 | 974.97 | 507.72 |
| 312.27 | 6827.28 | 456.37 | 10906.50 | 583.60 | 1347.17 | 735.76 | 745.74 | 975.80 | 512.98 |
| 313.18 | 3605.86 | 456.46 | 6082.07 | 584.34 | 1594.77 | 736.57 | 1355.25 | 976.80 | 611.92 |
| 313.27 | 3988.31 | 457.19 | 1278.43 | 584.44 | 2532.57 | 736.69 | 1673.39 | 977.78 | 531.52 |
| 314.11 | 3348.65 | 457.28 | 2532.32 | 584.53 | 2715.68 | 736.77 | 896.04 | 978.80 | 624.64 |
| 314.19 | 10946.24 | 457.37 | 5374.60 | 584.61 | 1016.35 | 737.57 | 1057.52 | 979.80 | 535.54 |
| 314.29 | 9588.88 | 457.46 | 2834.53 | 585.35 | 1199.42 | 737.70 | 1208.70 | 980.81 | 592.15 |
| 315.19 | 5063.77 | 458.20 | 2015.07 | 585.44 | 1746.43 | 737.78 | 657.33 | 981.81 | 544.51 |
| 315.29 | 4197.24 | 458.29 | 3919.58 | 585.53 | 1734.07 | 738.58 | 1401.51 | 982.80 | 561.45 |
| 316.12 | 6020.81 | 458.38 | 4959.38 | 586.36 | 1764.92 | 738.70 | 1171.21 | 983.81 | 538.73 |
| 316.21 | 21212.71 | 458.47 | 1714.69 | 586.45 | 2798.42 | 739.58 | 1031.31 | 984.80 | 582.26 |
| 316.30 | 14076.84 | 459.21 | 1314.97 | 586.54 | 2228.18 | 739.71 | 866.02 | 985.81 | 516.70 |
| 317.13 | 4273.28 | 459.30 | 2327.58 | 587.36 | 1269.05 | 740.52 | 1152.44 | 986.81 | 580.25 |
| 317.21 | 7651.08 | 459.39 | 2749.45 | 587.46 | 2016.17 | 740.63 | 1376.51 | 987.82 | 510.56 |
| 317.30 | 5030.17 | 459.47 | 976.22 | 587.55 | 1588.52 | 740.72 | 962.28 | 988.82 | 578.55 |
| 318.05 | 1630.46 | 460.22 | 2040.55 | 588.37 | 2084.47 | 741.59 | 1117.51 | 989.81 | 499.90 |
| 318.14 | 8710.98 | 460.31 | 4173.20 | 588.47 | 3248.65 | 741.72 | 817.25 | 990.80 | 567.55 |
| 318.22 | 7945.96 | 460.40 | 4136.24 | 588.56 | 2288.34 | 742.54 | 1223.61 | 990.99 | 393.68 |
| 318.31 | 2520.63 | 460.49 | 1035.22 | 589.38 | 1453.31 | 742.64 | 1479.67 | 991.80 | 507.76 |
| 319.15 | 5186.81 | 461.22 | 1404.75 | 589.47 | 2379.29 | 742.73 | 999.56 | 992.81 | 569.75 |
| 319.23 | 3744.47 | 461.31 | 2565.81 | 589.56 | 1622.76 | 743.54 | 1011.06 | 993.81 | 503.89 |
| 319.32 | 1514.97 | 461.40 | 2597.31 | 590.30 | 1191.72 | 743.65 | 1193.28 | 994.82 | 569.92 |
| 320.14 | 10061.09 | 462.23 | 2723.45 | 590.39 | 2136.01 | 743.74 | 792.39 | 995.81 | 499.19 |
| 320.24 | 6775.50 | 462.32 | 5394.45 | 590.48 | 3463.30 | 744.61 | 1452.47 | 996.81 | 563.02 |
| 320.33 | 1605.11 | 462.41 | 4207.48 | 590.57 | 2164.10 | 744.75 | 920.74 | 997.82 | 498.61 |
| 321.16 | 7167.63 | 463.24 | 1729.49 | 591.39 | 1523.86 | 745.61 | 1092.55 | 998.83 | 549.83 |
| 321.24 | 3879.34 | 463.33 | 3514.80 | 591.49 | 2210.66 | 745.75 | 754.50 | 999.82 | 501.63 |
| 322.16 | 9597.49 | 463.42 | 2643.97 | 591.58 | 1530.00 | 746.55 | 1153.21 | 1000.82 | 557.14 |
| 322.25 | 7615.38 | 464.16 | 1163.01 | 592.31 | 1200.52 | 746.68 | 1417.46 | 1001.82 | 490.00 |
| 323.16 | 5420.21 | 464.25 | 3209.70 | 592.41 | 1945.39 | 746.76 | 934.17 | 1002.83 | 568.24 |
| 323.26 | 3798.38 | 464.34 | 6403.48 | 592.50 | 3037.90 | 747.62 | 1039.51 | 1003.83 | 517.08 |
| 323.32 | 1330.75 | 464.43 | 4063.38 | 592.59 | 2299.34 | 747.77 | 736.82 | 1004.83 | 561.37 |
| 324.10 | 3619.05 | 465.25 | 1879.76 | 593.40 | 1467.70 | 748.57 | 1222.75 | 1005.82 | 491.58 |
| 324.18 | 11808.50 | 465.34 | 3375.75 | 593.50 | 2035.71 | 748.69 | 1512.20 | 1006.82 | 552.86 |
| 324.27 | 6910.93 | 465.43 | 2600.57 | 593.59 | 1494.44 | 748.78 | 964.22 | 1007.83 | 488.86 |
| 325.18 | 4686.85 | 466.17 | 1247.90 | 594.33 | 1316.63 | 749.63 | 1128.51 | 1008.83 | 571.68 |
| 325.27 | 3892.25 | 466.26 | 2721.41 | 594.42 | 2155.57 | 749.78 | 686.19 | 1009.83 | 498.00 |
| 326.11 | 3228.34 | 466.35 | 4912.59 | 594.52 | 3673.38 | 750.58 | 1262.90 | 1010.83 | 575.04 |
| 326.19 | 6645.70 | 466.44 | 4226.00 | 594.60 | 2416.07 | 750.71 | 1523.85 | 1011.83 | 498.61 |

TABLE 6-continued

| m/z | intensity | m/z | intensity | m/z | intensity | m/z | intensity | m/z | intensity |
|---|---|---|---|---|---|---|---|---|---|
| 326.29 | 6891.81 | 467.27 | 1814.06 | 595.42 | 1639.38 | 750.80 | 782.54 | 1012.83 | 541.12 |
| 327.19 | 3450.21 | 467.36 | 2891.79 | 595.52 | 2351.67 | 751.58 | 1006.83 | 1013.83 | 471.83 |
| 327.29 | 3941.18 | 467.45 | 2749.02 | 595.61 | 1502.77 | 751.71 | 1094.69 | 1014.84 | 542.60 |
| 328.12 | 3455.51 | 468.27 | 3249.62 | 596.34 | 1519.35 | 751.80 | 569.74 | 1015.84 | 482.20 |
| 328.21 | 10314.38 | 468.37 | 6586.23 | 596.44 | 2458.26 | 752.59 | 1276.46 | 1016.85 | 546.48 |
| 328.30 | 9317.09 | 468.46 | 6038.59 | 596.53 | 4426.16 | 752.72 | 1071.66 | 1017.82 | 499.12 |
| 329.12 | 1911.59 | 469.28 | 2208.37 | 596.62 | 2187.13 | 753.59 | 967.53 | 1018.03 | 376.36 |
| 329.21 | 4704.82 | 469.37 | 3708.58 | 597.42 | 1681.76 | 753.72 | 801.88 | 1018.83 | 551.37 |
| 329.30 | 4276.17 | 469.46 | 2972.58 | 597.54 | 2690.16 | 754.60 | 1278.06 | 1019.02 | 390.44 |
| 330.13 | 5473.86 | 470.21 | 1891.12 | 597.62 | 1271.16 | 754.73 | 915.44 | 1019.84 | 488.39 |
| 330.23 | 19595.17 | 470.29 | 3762.98 | 598.36 | 1541.43 | 755.61 | 1099.08 | 1020.83 | 553.19 |
| 330.32 | 13442.04 | 470.39 | 9929.70 | 598.45 | 2438.81 | 755.74 | 732.35 | 1021.84 | 487.20 |
| 331.14 | 3406.08 | 470.48 | 5684.63 | 598.54 | 2514.53 | 756.61 | 1377.01 | 1022.85 | 555.21 |
| 331.23 | 7337.56 | 471.29 | 2415.33 | 598.63 | 914.79 | 756.75 | 932.20 | 1023.85 | 509.21 |
| 331.32 | 4810.04 | 471.39 | 4928.06 | 599.44 | 1699.67 | 757.62 | 1101.06 | 1024.85 | 530.10 |
| 332.06 | 2109.09 | 471.48 | 2684.52 | 599.55 | 1620.99 | 757.75 | 727.45 | 1025.85 | 459.73 |
| 332.15 | 5658.54 | 472.22 | 2068.39 | 599.64 | 636.62 | 758.55 | 1116.31 | 1026.85 | 534.47 |
| 332.24 | 7709.21 | 472.31 | 3755.81 | 600.37 | 1725.39 | 758.68 | 1363.96 | 1027.85 | 471.80 |
| 332.33 | 2473.12 | 472.40 | 4603.71 | 600.47 | 2684.02 | 758.76 | 871.20 | 1028.85 | 544.95 |
| 333.15 | 2817.41 | 472.49 | 1647.85 | 600.56 | 2058.94 | 759.62 | 1019.45 | 1029.85 | 473.57 |
| 333.24 | 3621.24 | 473.22 | 1301.22 | 601.45 | 1893.94 | 759.77 | 668.90 | 1030.85 | 543.35 |
| 333.34 | 1334.44 | 473.31 | 2228.01 | 601.56 | 1522.86 | 760.63 | 1283.23 | 1031.83 | 486.55 |
| 334.16 | 5830.93 | 473.40 | 2600.03 | 602.39 | 2053.45 | 760.78 | 890.22 | 1032.03 | 369.99 |
| 334.25 | 6164.77 | 473.49 | 932.94 | 602.48 | 2991.07 | 761.63 | 971.67 | 1032.85 | 503.22 |
| 334.34 | 1454.92 | 474.23 | 2077.18 | 602.57 | 2073.90 | 761.78 | 680.96 | 1033.85 | 480.16 |
| 335.16 | 3448.84 | 474.32 | 4057.57 | 603.39 | 1405.76 | 762.58 | 1159.93 | 1034.86 | 515.44 |
| 335.26 | 3501.91 | 474.41 | 3871.99 | 603.49 | 2150.02 | 762.71 | 1377.04 | 1035.86 | 479.80 |
| 336.18 | 7878.92 | 474.50 | 955.08 | 603.58 | 1534.20 | 762.79 | 853.78 | 1036.86 | 533.89 |
| 336.27 | 7085.74 | 475.24 | 1380.64 | 604.40 | 2073.28 | 763.58 | 942.02 | 1037.86 | 481.25 |
| 337.18 | 4715.10 | 475.33 | 2573.26 | 604.50 | 3211.75 | 763.71 | 1075.82 | 1038.86 | 498.78 |
| 337.27 | 3795.31 | 475.42 | 2513.72 | 604.59 | 2028.03 | 763.80 | 647.53 | 1039.85 | 455.32 |
| 337.33 | 1351.42 | 476.25 | 2669.38 | 605.40 | 1434.74 | 764.59 | 1181.34 | 1040.86 | 525.34 |
| 338.11 | 4042.41 | 476.34 | 5073.88 | 605.50 | 2022.52 | 764.72 | 1427.70 | 1041.86 | 442.48 |
| 338.19 | 11305.32 | 476.43 | 3848.81 | 605.59 | 1454.80 | 764.81 | 759.78 | 1042.86 | 522.10 |
| 338.29 | 6551.12 | 477.25 | 1704.60 | 606.33 | 1164.90 | 765.59 | 950.51 | 1043.86 | 465.74 |
| 339.19 | 4764.93 | 477.35 | 3389.52 | 606.42 | 1829.66 | 765.73 | 1036.33 | 1044.85 | 533.22 |
| 339.29 | 3777.78 | 477.43 | 2524.54 | 606.52 | 2871.10 | 765.82 | 527.05 | 1045.87 | 467.26 |
| 340.12 | 3272.60 | 478.18 | 1357.59 | 606.61 | 2106.12 | 766.60 | 1184.59 | 1046.86 | 511.69 |
| 340.21 | 6613.46 | 478.26 | 3085.14 | 607.42 | 1422.86 | 766.73 | 985.12 | 1047.86 | 462.80 |
| 340.30 | 6783.69 | 478.36 | 6082.52 | 607.52 | 1925.80 | 766.83 | 473.34 | 1048.86 | 492.89 |
| 341.13 | 1843.32 | 478.44 | 3792.14 | 607.61 | 1508.85 | 767.60 | 937.70 | 1049.86 | 473.11 |
| 341.21 | 3499.80 | 479.27 | 1892.32 | 608.34 | 1282.03 | 767.74 | 761.01 | 1050.87 | 504.58 |
| 341.30 | 3827.94 | 479.36 | 3324.13 | 608.44 | 2117.60 | 768.54 | 1043.59 | 1051.87 | 481.98 |
| 342.13 | 3478.71 | 479.45 | 2422.49 | 608.53 | 3372.88 | 768.66 | 1231.59 | 1052.87 | 501.67 |
| 342.23 | 10137.62 | 480.27 | 2614.21 | 608.62 | 2264.71 | 768.75 | 870.76 | 1053.87 | 455.74 |
| 342.32 | 8842.35 | 480.37 | 4828.68 | 609.43 | 1570.22 | 769.62 | 1000.33 | 1054.87 | 493.40 |
| 343.14 | 2059.93 | 480.46 | 4078.84 | 609.54 | 2240.30 | 769.76 | 734.95 | 1055.87 | 440.44 |
| 343.23 | 4841.82 | 481.28 | 1780.69 | 609.62 | 1388.58 | 770.56 | 1119.96 | 1056.88 | 497.71 |
| 343.32 | 3928.66 | 481.38 | 2822.13 | 610.36 | 1444.04 | 770.68 | 1271.40 | 1057.87 | 458.74 |
| 344.15 | 5067.55 | 481.47 | 2646.32 | 610.45 | 2320.63 | 770.76 | 843.14 | 1058.86 | 507.72 |
| 344.24 | 19209.74 | 482.20 | 1508.33 | 610.55 | 4048.69 | 771.63 | 1026.39 | 1059.06 | 391.18 |
| 344.33 | 11960.08 | 482.29 | 3076.32 | 610.64 | 2030.71 | 771.77 | 689.57 | 1059.88 | 431.26 |
| 345.16 | 3009.68 | 482.39 | 6353.38 | 611.44 | 1645.31 | 772.63 | 1240.48 | 1060.88 | 513.92 |
| 345.25 | 7377.19 | 482.48 | 5383.48 | 611.55 | 2565.37 | 772.78 | 806.38 | 1061.87 | 451.02 |
| 345.34 | 4483.17 | 483.29 | 2014.10 | 611.64 | 1204.39 | 773.64 | 992.38 | 1062.88 | 485.52 |
| 346.08 | 2225.23 | 483.39 | 3591.24 | 612.37 | 1520.86 | 773.79 | 674.06 | 1063.89 | 444.81 |
| 346.16 | 4957.60 | 483.48 | 2850.92 | 612.47 | 2332.88 | 774.64 | 1197.13 | 1064.88 | 477.77 |
| 346.25 | 7308.26 | 484.22 | 1980.80 | 612.56 | 2317.86 | 774.80 | 787.38 | 1065.88 | 431.20 |
| 346.34 | 2406.53 | 484.31 | 3685.41 | 612.65 | 879.48 | 775.64 | 951.23 | 1066.88 | 483.91 |
| 347.17 | 2438.51 | 484.40 | 9324.37 | 613.45 | 1634.03 | 775.80 | 646.55 | 1067.89 | 452.88 |
| 347.26 | 3489.65 | 484.49 | 5044.93 | 613.56 | 1512.09 | 776.65 | 1230.91 | 1068.89 | 476.97 |
| 347.35 | 1250.03 | 485.30 | 2358.67 | 614.39 | 1674.12 | 776.81 | 820.43 | 1069.89 | 420.14 |
| 348.18 | 5292.66 | 485.41 | 4786.98 | 614.48 | 2533.33 | 777.65 | 931.78 | 1070.88 | 503.57 |
| 348.27 | 6086.03 | 485.50 | 2405.85 | 614.57 | 1933.91 | 777.82 | 581.54 | 1071.89 | 440.90 |
| 348.36 | 1385.48 | 486.23 | 2084.48 | 615.39 | 1250.38 | 778.60 | 1131.44 | 1072.89 | 480.03 |
| 349.18 | 3138.96 | 486.32 | 3589.12 | 615.49 | 1848.24 | 778.74 | 1277.13 | 1073.89 | 446.88 |
| 349.28 | 3514.23 | 486.41 | 4357.78 | 615.58 | 1434.38 | 778.83 | 694.77 | 1074.89 | 484.75 |
| 350.11 | 2650.11 | 486.50 | 1568.79 | 616.40 | 1910.70 | 779.60 | 938.54 | 1075.89 | 441.82 |
| 350.19 | 7620.95 | 487.24 | 1411.23 | 616.50 | 2924.73 | 779.74 | 967.85 | 1076.89 | 472.61 |
| 350.29 | 7011.04 | 487.33 | 2235.58 | 616.59 | 1987.55 | 779.83 | 506.94 | 1077.91 | 418.70 |
| 351.20 | 4516.56 | 487.42 | 2571.12 | 617.41 | 1369.62 | 780.61 | 1097.77 | 1078.90 | 490.58 |
| 351.29 | 3890.68 | 487.50 | 932.67 | 617.51 | 2171.03 | 780.75 | 924.81 | 1079.90 | 426.39 |
| 352.12 | 4099.34 | 488.25 | 2099.70 | 617.59 | 1431.42 | 781.61 | 879.07 | 1080.90 | 472.69 |
| 352.21 | 10276.02 | 488.34 | 3993.96 | 618.41 | 2014.88 | 781.76 | 719.88 | 1081.90 | 440.24 |
| 352.30 | 6641.95 | 488.43 | 3424.32 | 618.52 | 3053.06 | 782.62 | 1155.48 | 1082.90 | 452.44 |
| 353.13 | 2346.51 | 488.52 | 925.30 | 618.60 | 1936.00 | 782.77 | 805.56 | 1083.90 | 422.75 |
| 353.21 | 4581.24 | 489.25 | 1465.72 | 619.42 | 1372.15 | 783.63 | 947.24 | 1084.91 | 461.83 |
| 353.31 | 3783.23 | 489.34 | 2539.46 | 619.52 | 1974.90 | 783.77 | 652.64 | 1085.91 | 430.78 |

TABLE 6-continued

| m/z | intensity | m/z | intensity | m/z | intensity | m/z | intensity | m/z | intensity |
|---|---|---|---|---|---|---|---|---|---|
| 354.13 | 3297.90 | 489.44 | 2331.38 | 619.61 | 1332.86 | 784.57 | 1056.14 | 1086.90 | 466.86 |
| 354.22 | 6506.00 | 490.26 | 2670.42 | 620.42 | 1837.90 | 784.69 | 1203.54 | 1087.90 | 442.17 |
| 354.32 | 6967.04 | 490.36 | 4904.69 | 620.53 | 2617.15 | 784.78 | 783.06 | 1088.89 | 445.91 |
| 355.14 | 1922.48 | 490.45 | 3463.38 | 620.62 | 1936.41 | 785.64 | 956.34 | 1089.91 | 418.63 |
| 355.23 | 3408.06 | 491.27 | 1750.47 | 621.43 | 1382.18 | 785.78 | 647.02 | 1090.91 | 483.12 |
| 355.32 | 3902.09 | 491.36 | 3238.20 | 621.54 | 1797.86 | 786.65 | 1185.37 | 1091.90 | 471.71 |
| 356.15 | 3595.00 | 491.45 | 2318.32 | 621.62 | 1371.62 | 786.80 | 771.47 | 1092.91 | 454.91 |
| 356.24 | 10009.60 | 492.19 | 1186.86 | 622.44 | 2031.53 | 787.64 | 907.19 | 1093.92 | 429.60 |
| 356.33 | 8303.14 | 492.28 | 2847.55 | 622.55 | 3150.32 | 787.80 | 625.99 | 1094.91 | 464.72 |
| 357.16 | 2211.33 | 492.37 | 5553.16 | 622.64 | 2036.94 | 788.65 | 1107.57 | 1095.90 | 420.41 |
| 357.25 | 4644.86 | 492.46 | 3508.49 | 623.44 | 1485.57 | 788.81 | 747.70 | 1096.92 | 462.20 |
| 357.34 | 3886.33 | 493.28 | 1813.62 | 623.55 | 2095.56 | 789.65 | 888.87 | 1097.92 | 417.83 |
| 358.17 | 4688.81 | 493.38 | 3117.23 | 623.64 | 1334.22 | 789.81 | 610.46 | 1098.92 | 460.19 |
| 358.26 | 17958.73 | 493.47 | 2336.15 | 624.37 | 1443.61 | 790.60 | 1029.68 | 1099.92 | 429.96 |
| 358.35 | 11111.63 | 494.20 | 1221.23 | 624.47 | 2182.25 | 790.74 | 1148.91 | 1100.92 | 462.44 |
| 359.17 | 2852.61 | 494.29 | 2488.54 | 624.56 | 3730.07 | 790.83 | 729.72 | 1101.91 | 432.12 |
| 359.26 | 7294.84 | 494.39 | 4501.38 | 624.65 | 1812.74 | 791.66 | 890.51 | 1102.93 | 464.16 |
| 359.35 | 4409.68 | 494.48 | 3718.40 | 625.46 | 1558.04 | 791.83 | 556.72 | 1103.91 | 414.71 |
| 360.09 | 2093.08 | 495.30 | 1726.10 | 625.57 | 2241.01 | 792.67 | 1056.52 | 1104.92 | 434.80 |
| 360.18 | 5040.85 | 495.39 | 2666.11 | 625.65 | 1132.41 | 792.76 | 1194.91 | 1105.92 | 412.60 |
| 360.27 | 7484.26 | 495.48 | 2325.41 | 626.39 | 1418.44 | 792.84 | 649.15 | 1106.93 | 441.38 |
| 360.36 | 2340.83 | 496.22 | 1436.62 | 626.48 | 2164.63 | 793.62 | 876.94 | 1107.93 | 410.23 |
| 361.18 | 2661.25 | 496.31 | 3013.63 | 626.57 | 2074.60 | 793.76 | 881.84 | 1108.92 | 445.08 |
| 361.27 | 3474.47 | 496.40 | 5980.25 | 626.66 | 826.68 | 793.84 | 481.39 | 1109.92 | 405.51 |
| 361.37 | 1257.23 | 496.49 | 4509.68 | 627.47 | 1508.61 | 794.62 | 1074.20 | 1110.94 | 434.19 |
| 362.11 | 1463.50 | 497.31 | 2068.16 | 627.58 | 1428.12 | 794.77 | 862.61 | 1111.93 | 398.58 |
| 362.19 | 6708.23 | 497.41 | 3449.27 | 628.40 | 1496.86 | 795.63 | 851.14 | 1112.93 | 437.03 |
| 362.29 | 6286.62 | 497.50 | 2516.79 | 628.50 | 2354.47 | 795.77 | 660.57 | 1113.94 | 408.60 |
| 362.38 | 1361.73 | 498.24 | 1846.12 | 628.59 | 1848.04 | 796.64 | 1064.06 | 1114.93 | 433.38 |
| 363.20 | 4080.72 | 498.33 | 3380.70 | 629.49 | 1770.71 | 796.78 | 770.88 | 1115.93 | 395.41 |
| 363.29 | 3561.78 | 498.42 | 8496.22 | 629.59 | 1379.10 | 797.64 | 895.11 | 1116.93 | 441.05 |
| 364.12 | 2752.53 | 498.51 | 4448.25 | 630.42 | 1823.53 | 797.79 | 594.49 | 1117.94 | 408.45 |
| 364.21 | 10074.00 | 499.24 | 1301.71 | 630.52 | 2608.45 | 798.65 | 1089.62 | 1118.93 | 422.53 |
| 364.30 | 7481.44 | 499.33 | 2340.21 | 630.60 | 1868.72 | 798.80 | 752.18 | 1119.93 | 396.48 |
| 365.21 | 6023.51 | 499.42 | 4438.54 | 631.42 | 1329.07 | 799.65 | 907.26 | 1120.94 | 434.13 |
| 365.31 | 8627.61 | 499.51 | 2248.93 | 631.52 | 1997.67 | 799.80 | 602.64 | 1121.94 | 399.78 |
| 366.14 | 4076.87 | 500.25 | 1996.10 | 631.61 | 1350.32 | 800.66 | 1082.81 | 1122.94 | 428.29 |
| 366.23 | 10763.69 | 500.34 | 3568.92 | 632.43 | 1826.90 | 800.81 | 714.06 | 1123.94 | 401.72 |
| 366.32 | 8389.68 | 500.43 | 4068.49 | 632.53 | 2770.15 | 801.66 | 875.26 | 1124.95 | 417.06 |
| 367.16 | 2461.52 | 500.51 | 1385.82 | 632.62 | 1781.04 | 801.82 | 570.09 | 1125.94 | 384.34 |
| 367.23 | 4779.64 | 501.25 | 1375.69 | 633.43 | 1338.12 | 802.66 | 1038.97 | 1126.95 | 421.76 |
| 367.32 | 4377.69 | 501.35 | 2196.20 | 633.54 | 1843.12 | 802.83 | 689.32 | 1127.95 | 392.61 |
| 368.15 | 3215.36 | 501.43 | 2372.98 | 633.62 | 1244.87 | 803.66 | 817.93 | 1128.95 | 427.17 |
| 368.24 | 6477.14 | 501.52 | 837.77 | 634.44 | 1714.88 | 803.83 | 563.05 | 1129.95 | 397.75 |
| 368.33 | 7661.85 | 502.26 | 2104.33 | 634.55 | 2507.05 | 804.67 | 1077.84 | 1130.95 | 411.37 |
| 369.16 | 1939.34 | 502.36 | 3877.67 | 634.64 | 1802.22 | 804.84 | 670.71 | 1131.94 | 393.93 |
| 369.25 | 3409.76 | 502.44 | 3179.11 | 635.44 | 1334.47 | 805.67 | 847.44 | 1132.95 | 414.32 |
| 369.34 | 4519.41 | 502.53 | 892.08 | 635.55 | 1738.72 | 805.85 | 521.65 | 1133.95 | 407.99 |
| 370.17 | 3730.97 | 503.27 | 1413.75 | 635.64 | 1276.92 | 806.63 | 1024.09 | 1134.95 | 404.64 |
| 370.26 | 9439.49 | 503.36 | 2477.92 | 636.45 | 1960.72 | 806.77 | 1073.80 | 1135.95 | 383.05 |
| 370.35 | 9226.68 | 503.45 | 2181.05 | 636.56 | 2865.21 | 806.86 | 569.02 | 1136.96 | 418.14 |
| 371.17 | 2378.66 | 504.28 | 2635.72 | 636.65 | 1870.32 | 807.68 | 840.97 | 1137.96 | 380.54 |
| 371.26 | 4638.68 | 504.37 | 4581.93 | 637.46 | 1424.35 | 808.64 | 986.09 | 1138.95 | 424.18 |
| 371.35 | 4210.49 | 504.46 | 3326.48 | 637.57 | 1934.42 | 808.78 | 814.97 | 1139.95 | 381.07 |
| 372.09 | 1546.12 | 505.28 | 1709.11 | 637.65 | 1234.73 | 809.64 | 780.46 | 1140.96 | 408.38 |
| 372.18 | 4686.90 | 505.38 | 3183.68 | 638.47 | 2091.83 | 809.79 | 604.24 | 1141.96 | 382.07 |
| 372.27 | 17591.93 | 505.47 | 2452.49 | 638.58 | 3305.89 | 810.65 | 1022.89 | 1142.95 | 421.72 |
| 372.36 | 11470.55 | 506.21 | 1154.16 | 638.67 | 1638.69 | 810.80 | 711.17 | 1143.96 | 398.23 |
| 373.19 | 2827.34 | 506.30 | 2793.12 | 639.47 | 1531.16 | 811.65 | 833.50 | 1144.96 | 419.01 |
| 373.28 | 7128.49 | 506.39 | 5275.16 | 639.58 | 2164.26 | 811.80 | 612.86 | 1145.96 | 372.91 |
| 373.37 | 4287.08 | 506.48 | 3338.11 | 639.67 | 1000.18 | 812.66 | 1014.26 | 1146.97 | 405.99 |
| 374.11 | 2188.37 | 507.30 | 1783.94 | 640.40 | 1409.61 | 812.81 | 695.56 | 1147.97 | 390.10 |
| 374.20 | 4935.22 | 507.39 | 2932.61 | 640.50 | 2059.41 | 813.66 | 855.70 | 1148.96 | 397.45 |
| 374.29 | 7402.18 | 507.48 | 2146.14 | 640.59 | 2092.58 | 813.81 | 565.50 | 1149.96 | 377.47 |
| 374.37 | 2259.69 | 508.30 | 2455.37 | 640.67 | 804.78 | 814.67 | 1028.00 | 1150.96 | 399.53 |
| 375.20 | 2700.19 | 508.40 | 4356.21 | 641.48 | 1474.93 | 814.83 | 657.11 | 1151.97 | 368.41 |
| 375.29 | 3470.32 | 508.49 | 3536.16 | 641.59 | 1395.30 | 815.66 | 785.60 | 1152.97 | 393.13 |
| 375.38 | 1230.65 | 509.31 | 1730.33 | 642.42 | 1500.96 | 815.83 | 544.40 | 1153.98 | 377.50 |
| 376.12 | 1767.90 | 509.41 | 2570.76 | 642.52 | 2273.43 | 816.68 | 989.97 | 1154.97 | 393.88 |
| 376.21 | 6657.02 | 509.50 | 2269.31 | 642.61 | 1712.69 | 816.84 | 673.56 | 1155.97 | 397.06 |
| 376.30 | 6096.46 | 510.23 | 1473.80 | 643.42 | 1177.22 | 817.67 | 767.11 | 1156.97 | 396.42 |
| 376.39 | 1400.11 | 510.33 | 2776.17 | 643.52 | 1631.76 | 817.85 | 524.76 | 1157.98 | 380.03 |
| 377.21 | 3874.72 | 510.42 | 5551.36 | 643.61 | 1279.54 | 818.68 | 974.31 | 1158.98 | 422.54 |
| 377.31 | 3596.56 | 510.51 | 4041.62 | 644.43 | 1742.64 | 818.86 | 602.01 | 1160.97 | 404.64 |
| 378.22 | 7960.56 | 511.32 | 1964.87 | 644.53 | 2498.87 | 819.68 | 802.55 | 1161.97 | 370.39 |
| 378.32 | 6833.55 | 511.42 | 3227.85 | 644.62 | 1692.67 | 819.86 | 503.57 | 1162.98 | 407.84 |
| 379.22 | 4763.41 | 511.51 | 2274.05 | 645.44 | 1302.10 | 820.64 | 962.54 | 1164.98 | 388.21 |
| 379.32 | 4954.84 | 512.25 | 1759.73 | 645.54 | 1810.48 | 820.79 | 970.74 | 1165.99 | 359.61 |

TABLE 6-continued

| m/z | intensity | m/z | intensity | m/z | intensity | m/z | intensity | m/z | intensity |
|---|---|---|---|---|---|---|---|---|---|
| 380.16 | 4919.11 | 512.34 | 3235.67 | 645.62 | 1271.28 | 820.88 | 535.26 | 1166.98 | 406.46 |
| 380.24 | 9563.75 | 512.43 | 7733.71 | 646.45 | 1766.73 | 821.68 | 794.65 | 1167.99 | 364.22 |
| 380.33 | 7145.03 | 512.52 | 3936.39 | 646.55 | 2524.55 | 821.88 | 412.93 | 1168.99 | 407.59 |
| 381.23 | 4511.10 | 513.25 | 1241.09 | 646.64 | 1615.43 | 822.65 | 937.21 | 1170.99 | 399.63 |
| 381.34 | 3952.22 | 513.35 | 2197.68 | 647.45 | 1301.51 | 822.80 | 775.03 | 1172.00 | 362.27 |
| 382.17 | 3477.32 | 513.44 | 4197.77 | 647.55 | 1656.85 | 823.65 | 767.96 | 1172.98 | 386.41 |
| 382.26 | 6115.84 | 513.53 | 2068.88 | 647.64 | 1228.21 | 823.80 | 596.12 | 1175.00 | 390.41 |
| 382.35 | 7060.41 | 514.26 | 1863.96 | 648.45 | 1629.27 | 824.66 | 945.39 | 1175.99 | 358.57 |
| 383.18 | 2183.15 | 514.36 | 3254.45 | 648.56 | 2345.94 | 824.81 | 666.12 | 1176.99 | 373.63 |
| 383.26 | 3247.90 | 514.45 | 3850.35 | 648.65 | 1673.22 | 825.67 | 790.69 | 1177.99 | 359.75 |
| 383.35 | 4115.59 | 514.53 | 1316.66 | 649.53 | 1620.59 | 825.82 | 546.04 | 1179.00 | 372.75 |
| 384.18 | 3685.11 | 515.27 | 1290.50 | 649.66 | 1251.06 | 826.67 | 994.45 | 1180.00 | 363.37 |
| 384.27 | 9027.00 | 515.36 | 2078.17 | 650.39 | 1209.99 | 826.83 | 648.68 | 1180.99 | 377.51 |
| 384.36 | 8049.69 | 515.45 | 2228.71 | 650.49 | 1758.69 | 827.68 | 805.96 | 1183.00 | 363.04 |
| 385.19 | 2347.50 | 515.54 | 830.84 | 650.58 | 2691.52 | 827.84 | 551.10 | 1185.01 | 381.29 |
| 385.28 | 4418.40 | 516.28 | 1974.61 | 650.67 | 1701.44 | 828.68 | 950.82 | 1187.02 | 385.46 |
| 385.37 | 4007.96 | 516.37 | 3751.34 | 651.47 | 1382.11 | 828.84 | 605.20 | 1189.02 | 374.15 |
| 386.11 | 1652.83 | 516.46 | 3046.73 | 651.58 | 1865.08 | 829.68 | 763.15 | 1190.01 | 354.04 |
| 386.20 | 4485.67 | 516.55 | 834.73 | 651.67 | 1152.18 | 829.84 | 529.39 | 1191.02 | 368.53 |
| 386.29 | 16348.04 | 517.28 | 1383.08 | 652.48 | 2011.48 | 830.68 | 865.15 | 1193.00 | 367.31 |
| 386.38 | 10444.44 | 517.38 | 2527.78 | 652.60 | 3038.83 | 830.86 | 607.97 | 1195.02 | 367.67 |
| 387.20 | 2715.89 | 517.47 | 2100.69 | 652.68 | 1505.45 | 831.68 | 730.21 | 1197.02 | 368.99 |
| 387.29 | 6763.10 | 518.29 | 2545.88 | 653.49 | 1465.01 | 831.86 | 512.40 | 1201.02 | 386.35 |
| 387.38 | 4154.47 | 518.39 | 4392.76 | 653.60 | 1986.53 | 832.64 | 899.11 | 1203.02 | 385.33 |
| 388.12 | 2082.01 | 518.48 | 3172.76 | 653.68 | 936.11 | 832.79 | 908.45 | 1205.03 | 370.70 |
| 388.21 | 4689.28 | 519.30 | 1638.31 | 654.42 | 1329.79 | 832.87 | 592.07 | 1207.01 | 364.32 |
| 388.30 | 6879.45 | 519.39 | 2947.23 | 654.52 | 1943.52 | 833.69 | 738.01 | 1209.03 | 366.26 |
| 388.39 | 2180.24 | | | | | | | | |

TABLE 7A

| Constants | Values | Variable | Values | Equation | Value |
|---|---|---|---|---|---|
| KCET | 2.20E+05 | — | — | KCET | 2.20E+05 |
| $X_1$CET | −7.52E+05 | DEN | 8.83E−01 | X1 * DEN | −6.64E+05 |
| $X_2$CET | 8.50E+05 | DEN^2 | 7.79E−01 | X2 * DEN^2 | 6.63E+05 |
| $X_3$CET | −3.19E+05 | DEN^3 | 6.88E−01 | X3 * DEN^3 | −2.20E+05 |
| $X_4$CET | 1.14E+01 | TOF − MSI | 5.39E+02 | X4 * TOF − MSI | 6.12E+03 |
| $X_5$CET | −1.37E−02 | TOF − MSI^2 | 2.91E+05 | X5 * TOF − MSI^2 | −3.99E+03 |
| $X_6$CET | 7.78E−06 | TOF − MSI^3 | 1.57E+08 | X6 * TOF − MSI^3 | 1.22E+03 |
| $X_7$CET | −3.97E+00 | DEN * TOF − MSI | 4.76E+02 | X7 * DEN * TOF − MSI | −1.89E+03 |
| Cetane Number | | | | CN | 58 |

TABLE 7B

| Constants | Values | Variable | Values | Equation | Value |
|---|---|---|---|---|---|
| KPPT | −1.33E+04 | — | — | KCET | −1.33E+04 |
| $X_1$PPT | 5.15E+04 | DEN | 8.83E−01 | X 1 * DEN | 4.55E+04 |
| $X_2$PPT | −4.94E+04 | DEN^2 | 7.79E−01 | X2 * DEN^2 | −3.85E+04 |
| $X_3$PPT | 1.26E+04 | DEN^3 | 6.88E−01 | X3 * DEN^3 | 8.66E+03 |
| $X_4$PPT | −2.58E+01 | TOF − MSI | 5.39E+02 | X4 * TOF − MSI | −1.39E+04 |
| $X_5$PPT | 3.32E−02 | TOF − MSI^2 | 2.91E+05 | X5 * TOF − MSI^2 | 9.65E+03 |
| $X_6$PPT | −2.32E−05 | TOF − MSI^3 | 1.57E+08 | X6 * TOF − MSI^3 | −3.63E+03 |
| $X_7$PPT | 1.16E+01 | DEN * TOF − MSI | 4.76E+02 | X7 * DEN * TOF − MSI | 5.50E+03 |
| Pour Point | | | | PPT | −11 |

TABLE 7C

| Constants | Values | Variable | Values | Equation | Value |
|---|---|---|---|---|---|
| KCPT | 5.62E+04 | — | — | KCET | 5.62E+04 |
| $X_1$CPT | −1.92E+05 | DEN | 8.83E−01 | X1 * DEN | −1.69E+05 |
| $X_2$CPT | 2.20E+05 | DEN^2 | 7.79E−01 | X2 * DEN^2 | 1.71E+05 |
| $X_3$CPT | −8.42E+04 | DEN^3 | 6.88E−01 | X3 * DEN^3 | −5.79E+04 |
| $X_4$CPT | −3.39E+00 | TOF − MSI | 5.39E+02 | X4 * TOF − MSI | −1.83E+03 |
| $X_5$CPT | 6.33E−03 | TOF − MSI^2 | 2.91E+05 | X5 * TOF − MSI^2 | 1.84E+03 |
| $X_6$CPT | −4.40E−06 | TOF − MSI^3 | 1.57E+08 | X6 * TOF − MSI^3 | −6.89E+02 |
| $X_7$CPT | 4.38E−01 | DEN * TOF − MSI | 4.76E+02 | X7 * DEN * TOF − MSI | 2.08E+02 |
| Cloud Point | | | | CPT | −11 |

TABLE 7D

| Constants | Values | Variable | Values | Equation | Value |
|---|---|---|---|---|---|
| KAP | 1.06E+05 | — | | KCET | 1.06E+05 |
| $X_1$AP | −3.65E+05 | DEN | 8.83E−01 | X1 * DEN | −3.23E+05 |
| $X_2$AP | 4.12E+05 | DEN^2 | 7.79E−01 | X2 * DEN^2 | 3.21E+05 |
| $X_3$AP | −1.54E+05 | DEN^3 | 6.88E−01 | X3 * DEN^3 | −1.06E+05 |
| $X_4$AP | 1.23E+01 | TOF − MSI | 5.39E+02 | X4 * TOF − MSI | 6.63E+03 |
| $X_5$AP | −2.00E−02 | TOF − MSI^2 | 2.91E+05 | X5 * TOF − MSI^2 | −5.80E+03 |
| $X_6$AP | 1.31E−05 | TOF − MSI^3 | 1.57E+08 | X6 * TOF − MSI^3 | 2.06E+03 |
| $X_7$AP | −2.52E+00 | DEN * TOF − MSI | 4.76E+02 | X7 * DEN * TOF − MSI | −1.20E+03 |
| Aniline Point | | | | AP | 66 |

TABLE 7E

| Constants | Values | Variable | Values | Equation | Value |
|---|---|---|---|---|---|
| KON | 1.74E+05 | — | | KCET | 1.74E+05 |
| $X_1$ON | −6.07E+05 | DEN | 8.83E−01 | X1 * DEN | −5.36E+05 |
| $X_2$ON | 7.04E+05 | DEN^2 | 7.79E−01 | X2 * DEN^2 | 5.48E+05 |
| $X_3$ON | −2.73E+05 | DEN^3 | 6.88E−01 | X3 * DEN^3 | −1.87E+05 |
| $X_4$ON | 2.78E+00 | TOF − MSI | 5.39E+02 | X4 * TOF − MSI | 1.50E+03 |
| $X_5$ON | −9.85E−03 | TOF − MSI^2 | 2.91E+05 | X5 * TOF − MSI^2 | −2.86E+03 |
| $X_6$ON | 6.76E−06 | TOF − MSI^3 | 1.57E+08 | X6 * TOF − MSI^3 | 1.06E+03 |
| $X_7$ON | 2.18E+00 | DEN * TOF − MSI | 4.76E+02 | X7 * DEN * TOF − MSI | 1.04E+03 |
| Octane Number | | | | Octane Number | 52 |

TABLE 7F

| Constants | Values | Variable | Values | Equation | Value |
|---|---|---|---|---|---|
| KAROM | 1.03E+05 | — | | KCET | 1.03E+05 |
| $X_1$AROM | −3.51E+05 | DEN | 8.83E−01 | X1 * DEN | −3.10E+05 |
| $X_2$AROM | 3.96E+05 | DEN^2 | 7.79E−01 | X2 * DEN^2 | 3.09E+05 |
| $X_3$AROM | −1.48E+05 | DEN^3 | 6.88E−01 | X3 * DEN^3 | −1.02E+05 |
| $X_4$AROM | 4.92E+00 | TOF − MSI | 5.39E+02 | X4 * TOF − MSI | 2.65E+03 |
| $X_5$AROM | −2.34E−03 | TOF − MSI^2 | 2.91E+05 | X5 * TOF − MSI^2 | −6.79E+02 |
| $X_6$AROM | 1.58E−06 | TOF − MSI^3 | 1.57E+08 | X6 * TOF − MSI^3 | 2.48E+02 |
| $X_7$AROM | −4.33E+00 | DEN * TOF − MSI | 4.76E+02 | X7 * DEN * TOF − MSI | −2.06E+03 |
| Aromatics | | | | AROM | 17 |

The invention claimed is:

1. A system for assigning an indicative property to a gas oil fraction or a naphtha fraction of an oil sample, wherein the oil sample is selected from the group consisting of crude oils, bitumens, heavy oils and shale oils, the system comprising:
  a time of flight mass spectrometer (TOF-MS) that outputs TOF-MS data;
  a non-volatile memory device that stores software program modules and data, the data including TOF-MS data representative of cumulative mass fraction data;
  a processor coupled to the memory device;
  a first software program module, executed by the processor, that processes TOF-MS data derived by the time of flight mass spectrometer from the crude oil sample, wherein the processing includes the calculation of an TOF-MS index (TOFMSI) as a weighted average of the TOF-MS data; and
  a second software program module that derives the indicative property of the gas oil fraction or the naphtha fraction, as a function of the TOFMSI and a density of the oil sample.

2. A method for operating a computer to assign an indicative property to a gas oil fraction or a naphtha fraction of an oil sample, wherein the oil sample is selected from the group consisting of crude oils, bitumens, heavy oils and shale oils, the method comprising:
  deriving from the oil sample time of flight mass spectrometry (TOF-MS) data from a time of flight mass spectrometer (TOF-MS), the TOF-MS data representative of cumulative mass fraction data;
  obtaining a density of the oil sample;
  entering into the computer the density of the oil sample and the TOF-MS data;
  calculating an TOF-MS index (TOFMSI) as a weighted average of the TOF-MS data; and
  deriving the indicative property gas oil fraction or the naphtha fraction as a function of the TOFMSI and the density of the oil sample.

3. A method for operating a computer to assign an indicative property to a gas oil fraction or a naphtha fraction of an oil sample, wherein the oil sample is selected from the group consisting of crude oils, bitumens, heavy oils and shale oils, the method comprising:
  deriving from the oil sample time of flight mass spectrometry (TOF-MS) data from a time of flight mass spectrometer (TOF-MS), the TOF-MS data representative of cumulative mass fraction data;
  obtaining a density of the oil sample;
  entering into the computer the density of the oil sample and the TOF-MS data;
  calculating an TOF-MS index (TOFMSI) as a weighted average of the TOF-MS data; and
  deriving the indicative property of the gas oil fraction, the naphtha fraction, or the oil sample as a function of the TOFMSI and the density of the oil sample.

4. The method as in claim 2, wherein the weighted average of the TOF-MS data is according to the equation $$(TOF-MSI) = \frac{\left[\sum_{x,y=5,10,20,30,40,50,60,70,80,90,95} M_x * W_y\right]}{\left[\sum_{y=5,10,20,30,40,50,60,70,80,90,95} W_y\right]},$$

where M=mass, and W=cumulative mass fraction.

5. The method of claim 2, wherein the oil sample is crude oil.

6. The method of claim 2, wherein the oil sample is obtained from an oil well, stabilizer, extractor, or distillation tower.

7. The method of claim 2, wherein the indicative property is a cetane number.

8. The method of claim 2, wherein the indicative property is a pour point.

9. The method of claim 2, wherein the indicative property is a cloud point.

10. The method of claim 2, wherein the indicative property is an aniline point.

11. The method of claim 2, wherein the indicative property is an octane number.

12. The method of claim 2, wherein plural indicative properties are calculated including at least two indicative properties selected from the group consisting of cetane number, pour point, cloud point, aniline point and octane number.

13. The method of claim 2, wherein the indicative property is of a gas oil fraction.

14. The method of claim 2, wherein the indicative property is of a naphtha fraction.

15. The method of claim 2, wherein the TOF-MS data is over a mass-to-charge ratio range of 90-3000 m/z.

16. The method as in claim 3, wherein the weighted average of the TOF-MS data is according to the equation $$(TOF-MSI) = \frac{\left[\sum_{x,y=5,10,20,30,40,50,60,70,80,90,95} M_x * W_y\right]}{\left[\sum_{y=5,10,20,30,40,50,60,70,80,90,95} W_y\right]},$$

where M=mass, and W=cumulative mass fraction.

17. The method of claim 3, wherein the oil sample is crude oil.

18. The method of claim 3, wherein the indicative property is a cetane number, a pour point, a cloud point, or an aniline point of a gas oil fraction.

19. The method of claim 3, wherein the indicative property is an octane number of a naphtha fraction.

20. The method of claim 3, wherein the TOF-MS data is over a mass-to-charge ratio range of 90-3000 m/z.

* * * * *